(12) United States Patent
Kasahara et al.

(10) Patent No.: US 10,238,774 B2
(45) Date of Patent: Mar. 26, 2019

(54) BIOLOGICAL IMPLANT

(71) Applicant: NGK SPARK PLUG CO., LTD., Nagoya-shi, Aichi (JP)

(72) Inventors: Shinjiro Kasahara, Konan (JP); Masaya Iwata, Komaki (JP); Takenori Sawamura, Nagoya (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 37 days.

(21) Appl. No.: 15/022,981

(22) PCT Filed: Sep. 3, 2014

(86) PCT No.: PCT/JP2014/073190
§ 371 (c)(1),
(2) Date: Mar. 18, 2016

(87) PCT Pub. No.: WO2015/045762
PCT Pub. Date: Apr. 2, 2015

(65) Prior Publication Data
US 2016/0228615 A1 Aug. 11, 2016

(30) Foreign Application Priority Data

Sep. 24, 2013 (JP) ................................. 2013-196539

(51) Int. Cl.
*A61L 27/56* (2006.01)
*A61L 27/18* (2006.01)
(Continued)

(52) U.S. Cl.
CPC ............... *A61L 27/56* (2013.01); *A61L 27/18* (2013.01); *A61L 27/54* (2013.01); *C08L 71/00* (2013.01); *A61L 2430/02* (2013.01)

(58) Field of Classification Search
CPC ...................................................... C08L 71/00
See application file for complete search history.

(56) References Cited

U.S. PATENT DOCUMENTS 5,489,306 A * 2/1996 Gorski ................ A61F 2/30767
623/23.55
8,530,560 B2 9/2013 Kerr et al.
(Continued)

FOREIGN PATENT DOCUMENTS

JP H01-232967 A 9/1989
JP 2820415 B2 8/1998
(Continued)

OTHER PUBLICATIONS

ISA/Japanese Patent Office, International Search Report issued in International Stage of subject Application (PCT/JP2014/073190), dated Dec. 16, 2014.

*Primary Examiner* — Bethany P Barham
*Assistant Examiner* — Dominic Lazaro
(74) *Attorney, Agent, or Firm* — Stites & Harbison, PLLC; Jeffrey A. Haeberlin

(57) ABSTRACT

Provided is a biological implant which exhibits high binding ability to a biological tissue after having been embedded in a living organism, which secures an appropriate strength depending on a site to which the implant is applied, and in which a micropore structural portion is less likely to be removed from a macropore structural portion. The biological implant includes a macropore structural portion which defines macropores of the biological implant, and a micropore structural portion which has micropores therein, the micropores having a pore size smaller than that of the macropores, the biological implant being characterized in that the macropore structural portion has substantially no pores therein; the micropore structural portion is provided on the surface of the macropore structural portion; the macropore structural portion and the micropore structural portion are formed of the same engineering plastic material;

(Continued)

and the macropore structural portion is formed of a single material.

6 Claims, 5 Drawing Sheets

(51) Int. Cl.
*A61L 27/54* (2006.01)
*C08L 71/00* (2006.01)

(56) References Cited

U.S. PATENT DOCUMENTS

| | | |
|---|---|---|
| 2005/0233454 A1 | 10/2005 | Nies et al. |
| 2007/0213835 A1* | 9/2007 | Wimmer .................. A61F 2/30 623/23.58 |
| 2010/0042226 A1* | 2/2010 | Nebosky .................. A61F 2/30 623/23.3 |
| 2010/0131074 A1 | 5/2010 | Shikinami |
| 2011/0022181 A1 | 1/2011 | Kasahara et al. |
| 2011/0045087 A1 | 2/2011 | Kerr |
| 2014/0207237 A1 | 7/2014 | Kerr et al. |

FOREIGN PATENT DOCUMENTS

| | | |
|---|---|---|
| JP | 2002-146086 A | 5/2002 |
| JP | 2002-541925 A | 12/2002 |
| JP | 3541218 B2 | 4/2004 |
| JP | 2005-528144 A | 9/2005 |
| JP | 2011-511128 A | 4/2011 |
| WO | 2007/032390 A1 | 3/2007 |
| WO | 2009/095960 A1 | 8/2009 |

\* cited by examiner

BIOLOGICAL IMPLANT

TECHNICAL FIELD

The present invention relates to a biological implant, and more particularly to a biological implant including a portion which defines macropores of the biological implant (hereinafter the portion may be referred to as "macropore structural portion") and a portion which has micropores therein (hereinafter the portion may be referred to as "micropore structural portion"), the micropore structural portion being provided on the surface of the macropore structural portion.

BACKGROUND ART

In recent years, artificial bone grafting for treatment of a bone defect of a patient has received attention, since this therapeutic method imposes less physical burden on the patient than autologous bone grafting for treatment of the bone defect, and does not involve problems associated with preparation of autologous bone grafts.

A bioceramic material such as hydroxyapatite has been known as a good artificial bone material, since it chemically binds to bone. Unfortunately, such a bioceramic material has low strength and poor impact resistance.

A metal material having very high strength, such as a titanium alloy or a cobalt-chromium alloy, has also been known as an artificial bone material. However, such a metal material probably causes, for example, metal allergy, and has a much higher elastic modulus than biological bone. Thus, when artificial bone formed of a metal material is transplanted to, for example, a bone defect, stress shielding may occur due to the difference in mechanical characteristics between the metal material and biological bone, resulting in absorption of bone around the bone defect, and weakening of the bone.

In recent years, a resin (e.g., engineering plastic) has received attention as a material which can solve the aforementioned problems and has mechanical characteristics similar to those of biological bone. For example, high-density polyethylene resin is suitable as an artificial bone material, because of its very low elasticity. Polyether ether ketone (PEEK) is also suitable as an artificial bone material, since it has mechanical characteristics similar to those of biological bone, and exhibits excellent biocompatibility.

As is well known in the art, the structure of artificial bone is an important factor in terms of its binding ability to biological bone. Thus, a method has been proposed which transforms the surface of a resin molded product or the entire molded product into a porous structure so that a biological tissue readily enters the molded product when it is embedded into a living organism.

For example, Patent Document 1 describes "A polymer compound porous composite structure characterized by comprising a first sponge-like polymer compound porous structure including, in its pores and surface portions, a second sponge-like polymer compound porous structure which is formed of a polymer compound different from that forming the first sponge-like polymer compound porous structure." (claim 1).

Patent Document 2 describes "A composition characterized by comprising a porous macro (gross) structure formed of a biodegradable polymer and having open voids, and a porous microstructure having a large surface area per unit weight and located in the open voids." (claim 1) and "A composition according to claim 1, wherein the porous microstructure is formed of a chemotactic ground substance." (claim 2).

Patent Document 3 describes "A biodegradable and biocompatible porous scaffold characterized by a substantially continuous polymer phase having a highly interconnected bimodal distribution of open pore sizes comprising rounded large open pores of about 50 to about 500 microns in diameter and rounded small open pores less than 20 microns in size, wherein said small pores are aligned in an orderly linear fashion within the walls of the large pores." (claim 1) and "The small pores are formed when the polymer solution undergoes phase separation under cooling." (paragraph 0037).

Patent Document 4 describes "A porous structure comprising a network of polymer granules that are melted together at contact points, a microporous surface structure on the granules, and a plurality of interstitial spaces between the polymer granules" (claim 24) and "The particles are mixed with β-TCP at a ratio of 90% polymer 10% β-TCP. The resulting powder mix includes polymer particles coated with β-TCP. The presence of β-TCP causes the particles to bead and to prevent flow at or above the melting point of the polymer. The final material defines an interconnecting porous polymer with β-TCP coating. In a selected embodiment, the β-TCP or other coating powder is later removed from exposed surfaces within pores via acid leaching, a selective solvent process, or another powder removal process. In this case, the surface is calcium poor." (paragraphs 0024 and 0025).

PRIOR ART DOCUMENT

Patent Document

Patent Document 1: Japanese Patent No. 3541218
Patent Document 2: Japanese Patent No. 2820415
Patent Document 3: Japanese Kohyo Patent Publication No. 2002-541925
Patent Document 4: Japanese Kohyo Patent Publication No. 2011-511128

SUMMARY OF THE INVENTION

Problems to be Solved by the Invention

In the structure disclosed in Patent Document 1 or 2, a porous macrostructure portion is formed of a material different from that of a porous microstructure portion disposed on the surface of the porous macrostucture portion, which may cause a problem in terms of adhesion between these portions. The porous scaffold disclosed in Patent Document 3 may exhibit insufficient strength due to large and small pores provided in the entire porous scaffold. The porous polymer structure disclosed in Patent Document 4 is formed by heating polymer particles coated with coating powder (e.g., β-TCP) at a temperature equal to or higher than the melting point of the polymer, to thereby interconnect the particles. However, even when the coating powder is removed from exposed surfaces of the resultant pores, the coating powder may remain between the connected polymer particles, resulting in insufficient connection between the particles.

An object of the present invention is to provide a biological implant which exhibits high binding ability to a biological tissue after having been embedded in a living organism, which secures an appropriate strength depending on a site to which the implant is applied, and in which a micropore structural portion is less likely to be removed from a macropore structural portion.

Means for Solving the Problems

Means for solving the aforementioned problems is:

(1) a biological implant comprising a macropore structural portion which defines macropores of the biological implant, and a micropore structural portion which has micropores therein, the micropores having a pore size smaller than that of the macropores, the biological implant being characterized in that the macropore structural portion has substantially no pores therein; the micropore structural portion is provided on the surface of the macropore structural portion; the macropore structural portion and the micropore structural portion are formed of the same engineering plastic material; and the macropore structural portion is formed of a single material.

Preferred modes of (1) are as follows.

(2) A biological implant according to (1) above, wherein the macropore structural portion has an irregular cross section.

(3) A biological implant according to (1) above, wherein the macropore structural portion is formed through a thermal melting-stacking method or a mesh stacking method.

(4) A biological implant according to any one of (1) to (3) above, wherein the engineering plastic material is polyether ether ketone.

(5) A biological implant according to any one of (1) to (4) above, wherein the macropores have a mean pore size of 100 μm to 3,000 μm.

(6) A biological implant according to any one of (1) to (5) above, wherein some of the macropores communicate with one another.

(7) A biological implant according to any one of (1) to (6) above, wherein the micropore structural portion supports a bioactive substance thereon.

Effects of the Invention

The biological implant provided by the present invention exhibits high binding ability to a biological tissue after having been embedded in a living organism, and secures an appropriate strength depending on a site to which the implant is applied. In the biological implant, the micropore structural portion is less likely to be removed from the macropore structural portion.

In particular, the biological implant of the present invention is a surface porous structure in which the micropore structural portion is provided on the surface of the macropore structural portion. Thus, when the biological implant is embedded in, for example, a bone defect of a living organism, a biological tissue (e.g., bone tissue) passes through the macropores and reaches a deep portion of the surface porous structure, and the biological tissue then enters the micropores, wherein a new biological tissue is generated. Therefore, the biological tissue is fixed in the interior of the biological implant, whereby the biological tissue is strongly bonded to the biological implant.

In the biological implant of the present invention, the macropore structural portion has substantially no pores therein. Thus, the biological implant can suppress a reduction in strength, as compared with the case of a biological implant which is entirely formed of a porous structure. Therefore, the biological implant can be applied to a site requiring a relatively high strength, and can secure an appropriate strength depending on a site to which the implant is applied.

In the biological implant of the present invention, the macropore structural portion and the micropore structural portion are formed of the same engineering plastic material. Specifically, the micropore structural portion is formed not by, for example, surface coating of the macropore structural portion, but by providing micropores in a surface portion of the macropore structural portion. Therefore, the micropore structural portion is less likely to be removed from the macropore structural portion.

In the biological implant of the present invention, the macropore structural portion is formed of a single material; i.e., solely an engineering plastic material. Therefore, the biological implant has no weak portion, and the entire biological implant can maintain an intended strength.

MODES FOR CARRYING OUT THE INVENTION

The biological implant of the present invention comprises a macropore structural portion which defines macropores of the biological implant, and a micropore structural portion which has micropores having a pore size smaller than that of the macropores, wherein the macropore structural portion has substantially no pores therein; the micropore structural portion is provided on the surface of the macropore structural portion; the macropore structural portion and the micropore structural portion are formed of the same engineering plastic material; and the macropore structural portion is formed of a single material.

First Embodiment

Figure 1:
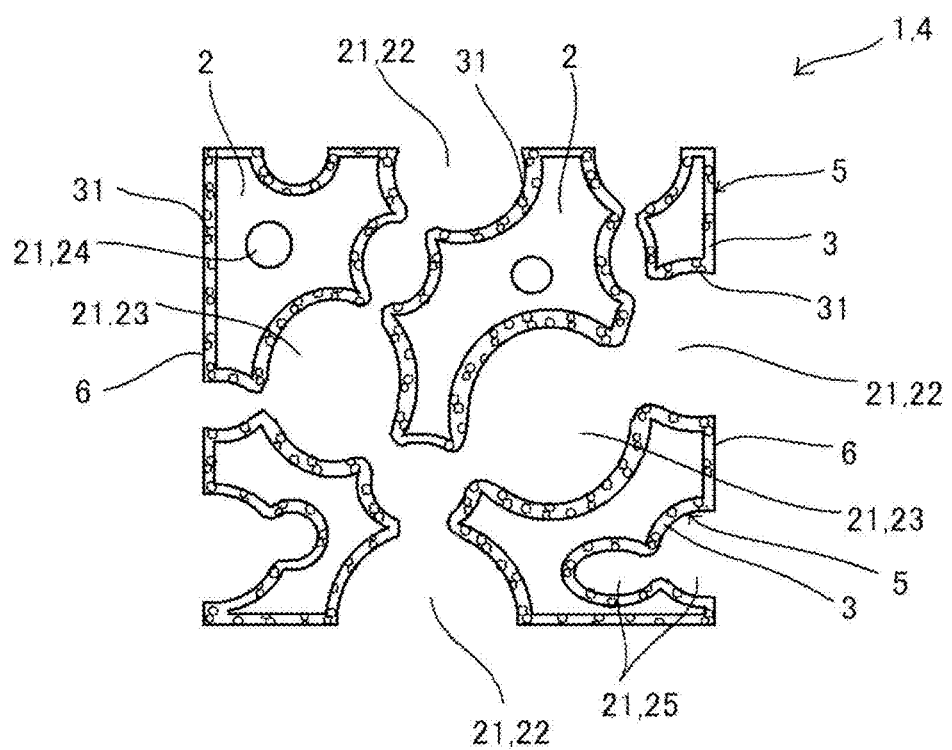
FIG. 1 schematically shows a cross section of an embodiment of the biological implant of the present invention.
Figure 2:
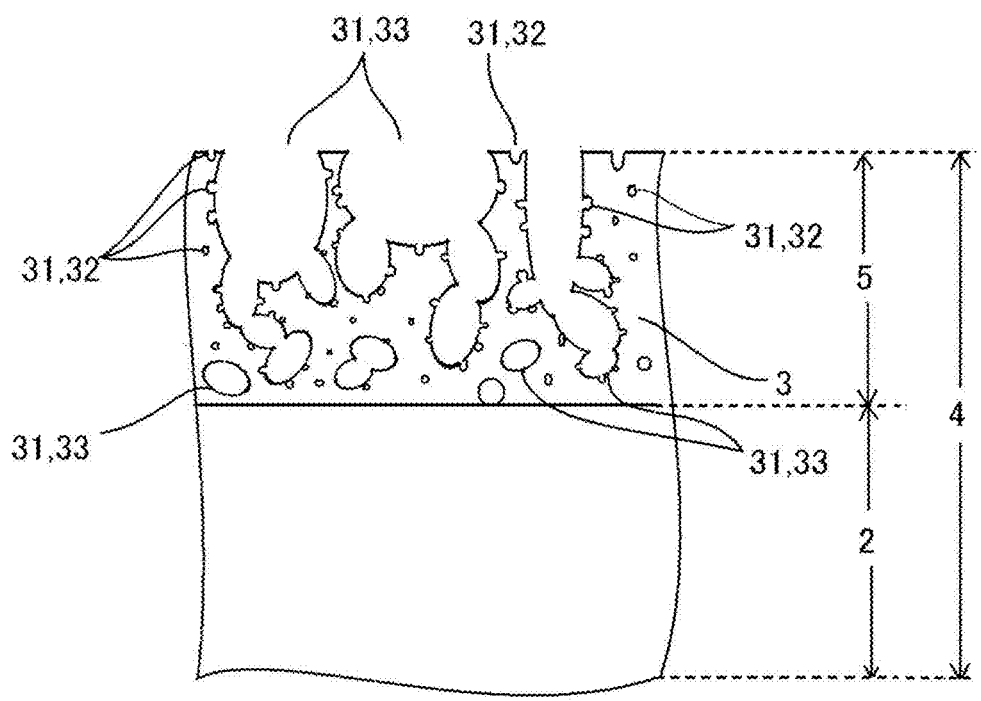
FIG. 2 is a schematic enlarged view of a microporous layer schematically shown in FIG. 1.

The biological implant of the present invention will next be described in detail with reference to FIGS. 1 and 2. FIG. 1 schematically shows a cross section of an embodiment of the biological implant of the present invention. FIG. 2 is a schematic enlarged view of a microporous layer schematically shown in FIG. 1. As shown in FIGS. 1 and 2, a biological implant 1 of the first embodiment is formed of a surface porous structure 4 including a macropore structural portion 2 which defines macropores 21, and a micropore structural portion 3 which has micropores 31 having a pore size smaller than that of the macropores 21. The macropore structural portion 2 has substantially no pores therein. The micropore structural portion 3 is provided on the surface of the macropore structural portion 2. The macropore structural portion 2 and the micropore structural portion 3 are integrally formed of the same engineering plastic material.

The macropore structural portion 2 defines a plurality of macropores 21 and serves as the skeleton of the surface porous structure 4 forming the biological implant 1. The entire macropore structural portion 2 is solid and formed of a single material, and has substantially no pores therein. Unlike the case of a biological implant which is entirely formed of a porous structure, the strength of the biological implant 1 can be widely adjusted by appropriately determining the volume, thickness, or the like of the macropore structural portion 2 of the biological implant 1. Therefore, the biological implant 1 can be applied to a site requiring a relatively high strength, and can secure an appropriate strength depending on a site to which the biological implant 1 is applied. Furthermore, since the macropore structural portion 2 is solid and formed of a single material (i.e., solely an engineering plastic material), the biological implant 1 has no weak portion, and the entire biological implant 1 can maintain an intended strength. As used herein, the expression "the macropore structural portion 2 has substantially no pores therein" refers to the case where pores are not intentionally provided in the macropore structural portion 2. Therefore, the macropore structural portion 2 may partially have hollows or pores, so long as most of the portion 2 is solid.

When the volume or thickness of the macropore structural portion 2 is increased, the strength of the biological implant 1 increases, but the porosity thereof decreases, resulting in a reduction in volume of spaces into which a biological tissue enters, leading to poor binding ability of the biological implant 1 to the biological tissue. In contrast, when the volume or thickness of the macropore structural portion 2 is decreased, the porosity of the biological implant 1 increases, resulting in an increase in volume of spaces into which a biological tissue enters. Thus, the biological implant 1 has improved binding ability to the biological tissue, but exhibits lowered strength. Therefore, the volume or thickness of the macropore structural portion 2 is appropriately determined in consideration of, for example, the strength required for a site to which the biological implant 1 is applied, or the required binding ability to a biological tissue.

The macropores 21 preferably have a mean pore size of 100 to 3,000 μm. When the biological implant 1 has macropores 21 having a mean pore size falling within the above range, a hard biological tissue (e.g., a bone tissue) readily enters the interior of the biological implant 1, and the biological implant 1 exhibits high binding ability to the biological tissue. The biological implant 1 may have macropores 21 having different pore sizes, or macropores 21 having a generally uniform pore size. When the biological implant 1 has macropores 21 having different pore sizes, an appropriate balance can be achieved between the size of a portion formed through communication of macropores and the strength of the biological implant. Thus, the biological implant allows a target biological tissue to enter the implant easily, and exhibits an appropriate strength against a site to which the implant is applied. In contrast, when the biological implant 1 has macropores 21 having a generally uniform pore size, the entire biological implant exhibits uniform strength, and the quality of the implant is readily controlled.

In the biological implant 1 of the first embodiment, macropores 21 having different pore sizes are distributed uniformly without being present unevenly. Therefore, the biological implant 1 has no weak portion, and the entire biological implant 1 can maintain an intended strength.

The macropores 21 are classified according to their states into open macropores 22 which are open at the surface of the biological implant 1, and inner macropores 23 which are present in the interior of the biological implant 1. Also, the macropores 21 are classified according to their states into independent macropores 24 which are independent of one another, and communicating macropores 25 which are provided through communication of macropores 21. In the first embodiment, the macropores 21 have a mean pore size of 100 to 3,000 μm. Thus, the open macropores 22 which are open at the surface of the biological implant 1 have a mean open pore size of 100 to 3,000 μm. The inner macropores 23 and the independent macropores 24 have a mean pore size of 100 to 3,000 μm. The communicating macropores 25 have a communicating pore size (i.e., the average of the sizes of communicating pores) of 100 to 3,000 μm. In the biological implant 1, preferably, communicating macropores 25 are provided through communication of a plurality of macropores 21, and the communicating macropores 25 communicate with the open macropores 22. In the case where the macropores 21 communicate with the open macropores 22 which are open at the surface of the biological implant 1, when the biological implant 1 has been embedded in a living organism, a biological tissue enters the interior of the biological implant 1 through the open macropores 22 which are open at the surface of the biological implant 1, and a new biological tissue is generated in the interior of the biological implant 1. Thus, the biological implant 1 is strongly bonded to the biological tissue.

The mean pore size of the macropores 21 can be determined through, for example, the intercept method on the basis of an image of a cross section of the biological implant 1 embedded in a resin (e.g., epoxy resin), the cross section being observed under a digital microscope. Specifically, a cross section of the biological implant 1 is observed under a digital microscope at a specific magnification (e.g., a magnification of 40), to thereby prepare an image. Five straight lines are randomly drawn across the image, and the macropores 21 on the straight lines are used for determination. The lengths of all the straight line segments on the macropores 21 are measured. The arithmetic mean of the thus-measured values are regarded as the mean pore size of the macropores 21.

The aforementioned image can be used for determination of the presence of macropores 21 having different pore sizes in the biological implant 1. When the image indicates that macropores having different pore sizes are generally entirely surrounded by the macropore structural portion 2, and/or non-uniform macropores whose shape is difficult to specify are present, the biological implant 1 has macropores 21 having different pore sizes.

Figure 4:
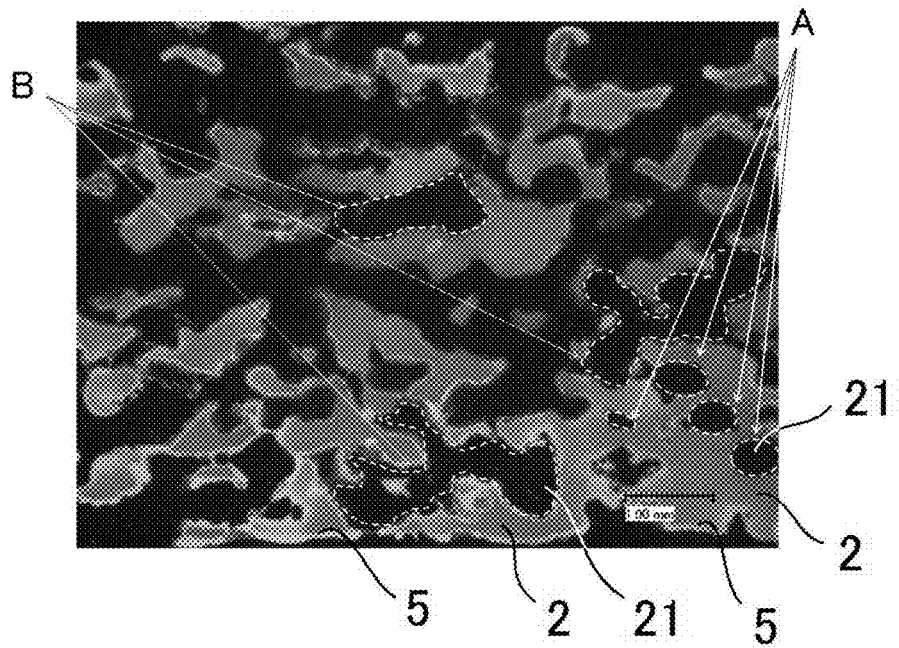
FIG. 4 shows an image of a cross section of a biological implant produced in Example 8, the cross section being observed under a digital microscope.

FIG. 4 shows a cross-sectional image of an example of the biological implant of the present invention. An exemplary form of macropores will be specifically described with reference to FIG. 4. As illustrated in the image of FIG. 4, the biological implant 1 has macropores 21 having different pore sizes. This image indicates that generally circular and generally elliptical pores (A) having different pore sizes are generally entirely surrounded by the macropore structural portion 2. This image also indicates the presence of pores (B) provided through communication of a plurality of irregular pores having different pore sizes; i.e., non-uniform macropores whose shape is difficult to specify. As described below, in the case of the biological implant of the first embodiment, a macroporous substrate having macropores 21 is formed through a pressure molding method. In the pressure molding method, engineering plastic particles are mixed with pore-providing material particles, and the resultant mixture is subjected to pressure molding and heating, followed by removal of the pore-providing material, to thereby provide macropores 21. For production of the biological implant of the first embodiment, the engineering plastic particles are melted and solidified during formation of the macroporous substrate, whereby the shape of the particles is lost. Therefore, the contour of the macropore structural portion 2 is defined by the pore-providing material, and the macropore structural portion 2 has an irregular cross section.

As show in FIGS. 1 and 2, the micropore structural portion 3 is provided on the surface of the macropore structural portion 2, and has therein micropores 31 having a pore size smaller than that of macropores 21. A microporous layer 5 having a porous structure is composed of a plurality of micropores 31 and the micropore structural portion 3. The biological implant 1, which is the surface porous structure 4, is composed of the macropores 21, the macropore structural portion 2, and the microporous layer 5. The microporous layer 5 is formed not by, for example, surface coating of the macroporous substrate, but by providing numerous micropores (i.e., by forming a porous structure) in a surface portion of the macroporous substrate as described below. Thus, since the macropore structural portion 2 and the micropore structural portion 3 are integrally formed of the same engineering plastic material, the micropore structural portion 3 is less likely to be removed from the macropore structural portion 2. When the micropore structural portion 3 is provided on the surface of the macropore structural portion 2, a biological tissue entering the macropores 21 enters the micropores 31, and a new biological tissue is generated in the microporous layer 5 serving as a scaffold. Thus, the biological tissue is fixed in the biological implant 1, and the biological tissue is strongly bonded to the biological implant. Therefore, even when, for example, the biological implant 1 is used as a biological implant for alveolar bone osteogenesis, and a pilot hole is drilled in the biological implant 1 for insertion of an artificial dental root, since the micropore structural portion 3 is less likely to be removed from the macropore structural portion 2, the biological implant 1 functions as a scaffold for generation of a new biological tissue, and the biological implant 1 is strongly bonded to the alveolar bone.

The micropore structural portion 3 may be provided on the entire surface of the macropore structural portion 2; i.e., the entire wall surfaces of the macropores 21 and the entire exposed surface 6 of the biological implant 1, so as to cover the macropore structural portion 2. Alternatively, the micropore structural portion 3 may be provided on a portion of the surface of the macropore structural portion 2; i.e., only on a surface of the macropore structural portion 2 that is required to be bonded to biological bone. For example, the micropore structural portion 3 may be provided only on the exposed surface 6 of the biological implant 1 and on the wall surfaces of the macropores 21 present in the vicinity of the exposed surface 6.

The micropores 31 preferably include small-size pores 32 having a mean pore size of less than 10 μm and medium-size pores 33 having a mean pore size of 10 to 200 μm. The microporous layer 5 preferably has a porous structure including a plurality of small-size pores 32 and a plurality of medium-size pores 33. Particularly, the microporous layer 5 preferably has a network structure including communicating medium-size pores provided through communication of a plurality of medium-size pores 33. When the microporous layer 5 has a network structure including small-size pores and medium-size pores, the microporous layer 5 serves as a scaffold for a biological tissue entering the macropores 21, and the microporous layer 5 readily and strongly bonded to the biological tissue.

The small-size pores 32 are classified according to their positions into open small-size pores which are open at the exposed surface 6 or the wall surfaces of the macropores 21, and inner small-size pores which are present in the interior of the microporous layer 5. Also, the small-size pores 32 are classified according to their states into independent small-size pores which are independent of one another, and communicating small-size pores which are provided through communication of small-size pores or which communicate with medium-size pores. The small-size pores 32 have a mean pore size of less than 10 μm. Thus, the open small-size pores have a mean open pore size of less than 10 μm, preferably 5 μm or less, particularly preferably 3 μm or less. The inner small-size pores and the independent small-size pores have a mean pore size of less than 10 μm, preferably 5 μm or less, particularly preferably 3 μm or less. The communicating small-size pores have a communicating pore size (i.e., the average of the sizes of communicating pores) of less than 10 μm, preferably 5 μm or less, particularly preferably 3 μm or less.

The medium-size pores 33 are classified according to their positions into open medium-size pores which are open at the exposed surface 6 or the wall surfaces of the macropores 21, and inner medium-size pores which are present in the interior of the microporous layer 5. Also, the medium-size pores 33 are classified according to their states into independent medium-size pores which are independent of one another, communicating medium-size pores which communicate with open medium-size pores, and communicating closed medium-size pores which are provided through communication of medium-size pores and which do not communicate with open medium-size pores. The medium-size pores 33 have a mean pore size of 10 to 200 μm. Thus, the open medium-size pores have a mean open pore size of 10 to 200 μm, preferably 30 to 150 μm. The inner medium-size pores and the independent medium-size pores have a mean pore size of 10 to 200 μm, preferably 30 to 150 μm. The communicating medium-size pores and the communicating closed medium-size pores have a communicating medium pore size (i.e., the average of the sizes of communicating medium pores) of 10 to 200 μm, preferably 30 to 150 μm.

The mean open pore size of open small-size pores or the mean open pore size of open medium-size pores can be determined through, for example, the aforementioned intercept method on the basis of an image of the surface of the biological implant 1 observed under a scanning electron microscope. Specifically, for the mean open pore size of open medium-size pores, the surface of the biological implant 1 is observed under a scanning electron microscope at a specific magnification (e.g., a magnification of 300), to thereby prepare an SEM image. Five straight lines are randomly drawn across the image, and the open medium-size pores on the straight lines are used for determination. The lengths of all the straight line segments on the open medium-size pores are measured. The arithmetic mean of the thus-measured values are regarded as the mean pore size of the open medium-size pores. Meanwhile, since open small-size pores are generally present in a portion between open medium-size pores, the mean open pore size of open small-size pores is preferably determined by increasing the magnification of a scanning electron microscope for reducing measurement error. For example, the mean open pore size of open small-size pores is determined through the intercept method on the basis of an SEM image obtained by observation under a scanning electron microscope at a magnification of 3,000.

When the number of open medium-size pores or open small-size pores found in an SEM image is small (e.g., 10 or less), all the major-axis and minor-axis lengths of open medium-size pores or open small-size pores found in the SEM image may be measured, and the arithmetic mean of the thus-measured values may be regarded as the mean open pore size of the open medium-size pores or open small-size pores.

The mean pore size of inner medium-size pores or independent medium-size pores, or the mean pore size of inner small-size pores or independent small-size pores can be determined in the same manner as the aforementioned mean open pore size through observation of any cross section of the biological implant 1 under a scanning electron microscope.

The communicating pore size of communicating medium-size pores or communicating closed medium-size pores, or the communicating pore size of communicating small-size pores can be determined in the same manner as described above on the basis of an SEM image obtained at a specific magnification. Alternatively, the communicating pore size may be determined by means of a mercury porosimeter.

The thickness of the microporous layer 5 is appropriately determined in consideration of a site to which the biological implant 1 is applied, or the required strength or binding ability of the biological implant 1 to a biological tissue. The thickness of the microporous layer 5 is preferably 20 to 500 μm. When the thickness of the microporous layer 5 falls within the above range, the microporous layer 5 readily serves as a scaffold for a biological tissue entering the macropores 21, and the microporous layer 5 exhibits high binding ability of the biological tissue. The thickness of the microporous layer 5 can be determined as follows. Specifically, a cross section of the microporous layer 5 is observed under a scanning electron microscope, and the distance between the deepest point of the micropores 31 and the exposed surface 6 or the wall surfaces of the macropores 21 is measured by use of the resultant SEM image. The thus-measured value is regarded as the thickness of the microporous layer 5 at the measurement point.

The biological implant 1 preferably has a porosity of 30 to 90%. When the porosity of the biological implant 1 falls within the above range, the biological implant 1 can secure a space into which a biological tissue enters. Therefore, the biological implant 1 exhibits high binding ability to a biological tissue after having been embedded in a living organism, and secures an appropriate strength depending on a site to which the implant is applied. The porosity can be calculated on the basis of the mass and volume of the biological implant 1 and the specific weight of the material forming the biological implant 1.

The material forming the biological implant 1 preferably has mechanical characteristics similar or approximate to those of biological bone or tooth. The mechanical characteristics similar or approximate to those of biological bone or tooth are, for example, an elastic modulus of 1 to 50 GPa and a flexural strength of 100 MPa or more. The material preferably has at least one of these characteristics.

The material forming the biological implant 1 is an engineering plastic material. The engineering plastic material is preferably one having mechanical characteristics similar or approximate to those of biological bone or tooth. Examples of the engineering plastic material include aromatic polyether ketones, such as polyether ether ketone, polyether ether ketone ketone, polyether ketone ketone, and polyether ketone ether ketone ketone; thermoplastic engineering plastic materials, such as polyamide, polyacetal, polycarbonate, polyphenylene ether, modified polyphenylene ether, polyester, polyphenylene oxide, polybutylene terephthalate, polyethylene terephthalate, polysulfone, syndiotactic polystyrene, polyethersulfone, polyphenylene sulfide, polyarylate, polyetherimide, polyamideimide, fluororesin, ethylene-vinyl alcohol copolymer, polymethylpentene, diallyl phthalate resin, polyoxymethylene, and polyethylene tetrafluoride; and thermosetting engineering plastic materials, such as phenolic resin, urea resin, melamine resin, unsaturated polyester, epoxy resin, diallyl phthalate, silicone resin, and polyurethane.

Of these, the material forming the macropore structural portion 2 is particularly preferably polyether ether ketone (PEEK), which has mechanical characteristics similar to those of biological bone and has high biocompatibility.

The aforementioned engineering plastic material may be fiber-reinforced engineering plastic material containing fiber. Examples of the fiber incorporated into the fiber-reinforced engineering plastic material include carbon fiber such as carbon nanotube, glass fiber, ceramic fiber, metal fiber, and organic fiber. Examples of the glass fiber include borosilicate glass (E-glass) fiber, high-strength glass (S-glass) fiber, and highly elastic glass (YM-31A glass) fiber. Examples of the ceramic fiber include silicon carbide fiber, silicon nitride fiber, alumina fiber, potassium titanate fiber, boron carbide fiber, magnesium oxide fiber, zinc oxide fiber, aluminum borate fiber, and boron fiber. Examples of the metal fiber include tungsten fiber, molybdenum fiber, stainless steel fiber, steel fiber, and tantalum fiber. Examples of the organic fiber include polyvinyl alcohol fiber, polyamide fiber, polyethylene terephthalate fiber, polyester fiber, and aramid fiber. These fibers may be employed singly or in combination of two or more species.

The macropore structural portion 2 may optionally contain, in addition to the engineering plastic material, an additive, such as an antistatic agent, an antioxidant, a photostabilizer (e.g., a hindered amine compound), a lubricant, an antiblocking agent, an ultraviolet absorber, an inorganic filler, or a colorant (e.g., a pigment).

When the biological implant 1 is used as a biological implant for alveolar bone osteogenesis, a pilot hole is drilled in the biological implant 1 for insertion of an artificial dental root after alveolar bone osteogenesis. Thus, the biological implant 1 preferably has such a strength that a pilot hole is readily drilled, and the biological implant 1 does not break during drilling of the pilot hole. This property of the biological implant 1 can be evaluated on the basis of the maximum torque and the maximum load during drilling of a pilot hole in the biological implant 1. In the case where the biological implant 1 is used as a biological implant for alveolar bone osteogenesis, when a pilot hole is provided with a drill having a diameter of 3.2 mm, the maximum torque is preferably 2 to 20 N·cm, and the maximum load is preferably 5 to 50 N. The maximum torque or the maximum load can be adjusted by appropriately setting, for example, the pore size of the macropores 21 or the porosity of the biological implant 1.

The maximum torque can be determined as follows. Specifically, a test piece of the biological implant 1 is prepared, and the test piece is placed on a testing table. A hole is drilled in the test piece with a drill (diameter: 3.2 mm) provided in a dental drill engine and rotated at 800 rpm.

The maximum of torque of the drill is measured during drilling with the dental drill engine, and the thus-measured value can be regarded as the maximum torque.

The maximum load can be determined as follows. Specifically, a test piece of the biological implant 1 is prepared, and the test piece is placed on a load cell. A hole is drilled in the test piece with a drill (diameter: 3.2 mm) provided in a dental drill engine and rotated at 800 rpm. The maximum of load imposed on the load cell via the test piece is measured during drilling with the dental drill engine, and the thus-measured value can be regarded as the maximum load.

The biological implant 1 is suitable for use as a biological implant which is embedded or charged in, for example, a bone defect; specifically in the form of, for example, a bone prosthetic material, an artificial joint, a bone joining material, an artificial vertebral body, an intervertebral spacer, a vertebral cage, an artificial tooth root, or an alveolar bone osteogenic material. Particularly, the biological implant 1 is suitable for use as a biological implant which exhibits high binding ability to a biological tissue, and secures an appropriate strength depending on a site to which the implant is applied, wherein the micropore structural portion is less likely to be removed. Therefore, the biological implant 1 is suitable as a biological implant for alveolar bone osteogenesis.

The biological implant 1 is produced to have a desired shape. Alternatively, the biological implant 1 is produced to have an appropriate shape and then processed (e.g., cut or shaved) into a desired shape corresponding to a site to which the implant is applied. The desired shape may be, for example, the same shape as that of a site in which the implant is charged, or a shape corresponding to (e.g., similar to) that of the site. Specifically, the biological implant 1 is provided in the form of, for example, granules, fiber, block, or film.

The biological implant 1 is produced through, for example, the following procedure.

The surface porous structure 4 serving as the biological implant 1 is produced through process 1 of forming a macroporous substrate which defines a plurality of macropores 21, and process 2 of forming, in a surface portion of the macroporous substrate, a micropore structural portion 3 which has micropores 31 therein.

In process 1, the macroporous substrate defining macropores 21 is produced through, for example, any of the following methods:

(1) a method in which engineering plastic particles are mixed with a pore-providing material, the mixture is subjected to molding and heating, and the pore-providing material is removed for providing macropores 21, to thereby produce a macroporous substrate (pressure molding method);

(2) a method in which engineering plastic particles are welded together for providing macropores 21 between the particles, to thereby produce a macroporous substrate (granule joining method);

(3) a method in which a melted engineering plastic material is extruded through a nozzle, to thereby produce a macroporous substrate (thermal melting-stacking method); and (4) a method in which mesh sheets are stacked, to thereby produce a macroporous substrate (mesh stacking method).

Now will be described process 1 of producing a macroporous substrate by the pressure molding method (1).

Process 1 includes step (a) of preparing engineering plastic particles forming the biological implant 1 and particles of a soluble material serving as a pore-providing material, so that the particles have a desired particle size; step (b) of mixing the respective particles prepared in step (a) in specific proportions, to thereby prepare a mixture; step (c) of subjecting the mixture to pressure molding, to thereby form a molded product; step (d) of heating the molded product, to thereby prepare a heated molded product; and step (e) of immersing the heated molded product in a solvent capable of dissolving the soluble material, to thereby elute the soluble material and to produce a macroporous substrate.

Step (a) involves preparation of engineering plastic particles and particles of a soluble material serving as a pore-providing material. The engineering plastic material may be at least one of the aforementioned engineering plastic materials, and may contain fiber. No particular limitation is imposed on the soluble material, so long as it can dissolve in any of the below-described solvents and does not melt or decompose during heating of a molded product in step (d). For example, when the solvent is an aqueous solvent, the soluble material may be a water-soluble compound, whereas when the solvent is an organic solvent, the soluble material may be an organic compound. Examples of the water-soluble compound include sugars, celluloses, proteins, inorganic compounds, polyvinyl alcohol, polyvinyl pyrrolidone, polyacrylic acid, polyacrylic acid salts, polyethylene oxide, sulfonated polyisoprene, and sulfonated polyisoprene copolymers. Examples of the sugar include polysaccharides, such as α-cyclodextrin, β-cyclodextrin, γ-cyclodextrin, dextrin, and starch, sucrose, maltose, lactose, and mannitol. Examples of the cellulose include hydroxypropylcellulose and methylcellulose. Examples of the inorganic compound include salts, such as sodium chloride and potassium chloride. Examples of the organic compound include resins, such as polyacrylic acid esters and polymethacrylic acid esters. These soluble materials may be employed singly or in combination of two or more species.

The engineering plastic particles or the soluble material particles preferably have a particle size of 100 to 1,000 μm. The soluble material is eluted in step (e), and voids resulting from the elution provide most of the macropores 21. Thus, the pore size of the macropores 21 can be adjusted by appropriately determining the particle size of the soluble material particles. The porosity of the biological implant 1 can be increased by increasing the ratio of the soluble material particles to the engineering plastic particles. The engineering plastic particles and the soluble material particles may have the same particle size or different particle sizes.

No particular limitation is imposed on the method for preparing the engineering plastic particles or the soluble material particles. Examples of the preparation method include a method in which a granular or powdery engineering plastic or soluble raw material is subjected to sieve classification, to thereby prepare particles having a desired particle size; a method in which a fibrous or tubular engineering plastic or soluble material is cut into columnar or tubular particles having an appropriate length; and a method in which a bulky engineering plastic or soluble material is pulverized or crushed to form granules or powder, followed by sieve classification, to thereby prepare particles having a desired particle size.

Step (b) involves preparation of a mixture through mixing of the engineering plastic particles and the soluble material particles. No particular limitation is imposed on the method for mixing the engineering plastic particles with the soluble material particles, and a dry mixing method (e.g., a dry blend method) may be employed. The ratio of the volume of the soluble material particles to the total volume of the engineering plastic particles and the soluble material particles is preferably 30 to 90 vol %. Since most of the macropores 21 are provided through removal of the soluble material particles, when the volume ratio of the soluble material particles falls within the above range, the biological implant 1 is readily provided with desirable strength, binding ability to a biological tissue, and the like.

Step (c) involves formation of a molded product through pressure molding of the mixture prepared in step (b). No particular limitation is imposed on the molding method, and, for example, press molding with a mold may be employed. No particular limitation is imposed on the pressure during press molding, so long as the resultant molded product maintains its shape and can be processed in the subsequent step. The pressure is preferably 5 to 200 MPa. The temperature during press molding can be appropriately determined so as to fall within a range of ambient temperature to a temperature lower than the melting point of the engineering plastic material.

Step (d) involves preparation of a heated molded product through heating of the molded product formed in step (c). The heating temperature and the heating time are appropriately determined so as to weld or melt the engineering plastic particles without causing melting or decomposition of the soluble material particles. When the engineering plastic material is polyether ether ketone, and the soluble material is sodium chloride, the heating temperature is preferably 340 to 380° C., and the heating time is preferably 5 to 60 minutes.

Step (e) involves immersion of the heated molded product prepared in step (d) in a solvent capable of dissolving the soluble material, to thereby elute the soluble material and to produce a macroporous substrate. No particular limitation is imposed on the immersion method of the heated molded product. For example, the heated molded product may be immersed in the solvent without any pretreatment, or the solvent may be stirred. Alternatively, a defoaming treatment may be carried out by reducing the pressure in a container containing the heated molded product and the solvent, so that the solvent enters the interior of the heated molded product. In this case, the amount of the heated molded product immersed in the solvent is not particularly limited, so long as the soluble material can be eluted. For example, the amount of the heated molded product is 1 to 10 mass % relative to the mass of the solvent. No particular limitation is imposed on the immersion conditions, and, for example, immersion may be carried out at room temperature until the soluble material is eluted.

The solvent is selected depending on the type of the soluble material. When, for example, the soluble material is a water-soluble compound, the solvent used is an aqueous solvent capable of dissolving the water-soluble compound, such as water, alcohol, or aqueous alcohol. Meanwhile, when the soluble material is an organic compound, the solvent used is an organic solvent which dissolves the organic compound but does not dissolve or alter the engineering plastic material; for example, acetone or isopropanol. Since the biological implant 1 is embedded in a living organism, the solvent is preferably an aqueous solvent, particularly preferably water.

When the heated molded product is immersed in the solvent, the soluble material contained in the heated molded product is gradually eluted, to thereby provide the macropores 21 and to produce a macroporous substrate having a porous structure with the skeleton remaining intact.

In step (c) and step (d), when the molding pressure is adjusted for preventing excessive collapse of the engineering plastic particles, and a mixture of the engineering plastic particles and the soluble material particles is subjected to pressure molding and then appropriately heated, the shape of the engineering plastic particles is maintained, and thus the resultant macroporous substrate is formed of joined engineering plastic particles. In this case, the macropores 21 are provided not only at voids resulting from elution of the soluble material, but also at voids provided between the engineering plastic particles. Thus, the macropores 21 have different shapes and sizes. In contrast, in step (c) and step (d), when a mixture of the engineering plastic particles and the soluble material particles is subjected to pressure molding at an appropriate pressure, and the molded product is heated at a temperature equal to or higher than the melting point of the engineering plastic material, the engineering plastic material is melted and then solidified, and thus the shape of the particles becomes unclear. Thus, the resultant macroporous substrate has an irregular cross section. Since spaces between the soluble material particles are filled with the melted and solidified engineering plastic material, the contour of the macroporous substrate is defined by the soluble material particles. In this case, the macropores 21 are provided at voids resulting from elution of the soluble material.

In process 1, step (e) may optionally be followed by a post-treatment step; such as a washing or drying step of the resultant macroporous substrate. The drying step may involve reduced-pressure drying or thermal drying at such a temperature that the macroporous substrate is not denatured.

In the production process including steps (a) to (e), step (c) (i.e., pressure molding of the mixture to form a molded product) and step (d) (i.e., heating of the molded product to prepare a heated molded product) may be modified to step (c') of subjecting the mixture prepared in step (b) to pressure molding (hot pressing) while heating the mixture, to thereby form a molded product. No particular limitation is imposed on the molding method in step (c'), and, for example, press molding with a mold may be carried out. For the press molding, the mixture is placed in the mold and heated to a specific temperature, and pressure is applied to the mold while the mold is maintained at the temperature. No particular limitation is imposed on the molding pressure and the molding temperature, so long as the engineering plastic particles are welded or melted. For example, the molding pressure may be 5 to 200 MPa, and the heating temperature may be equal to that employed in step (d).

The macroporous substrate, which is produced through the pressure molding method, is formed of a single material (i.e., solely the engineering plastic material), wherein voids resulting from the elution of the soluble material provide most of the macropores 21. Thus, the pore size distribution of the macropores 21 can be adjusted by appropriately determining the particle size of the soluble material particles. When, for example, soluble material particles having the same particle size are employed, the resultant macropores 21 tend to have the same pore size. When the mixture is subjected to press molding to form a molded product in step (c), depending on the molding pressure and the molding temperature, voids provided between the engineering plastic particles may serve as the macropores 21. Since the voids have different shapes and sizes, the macropores 21 have different shapes and sizes. Therefore, when the molding pressure and the molding temperature are appropriately determined, the macropores 21 having different shapes and sizes can be provided in addition to the macropores 21 resulting from elution of the soluble material.

Now will be described process 1 of producing a macroporous substrate by the granule joining method (2).

Process 1 includes step (A) of preparing engineering plastic particles having a desired particle size, the particles forming the biological implant 1; and step (B) of placing the particles prepared through step (A) into a mold and heating the particles, to thereby produce a macroporous substrate.

Step (A) involves preparation of engineering plastic particles. The engineering plastic material may be at least one of the aforementioned engineering plastic materials, and may contain fiber. The engineering plastic particles preferably have a particle size of 200 to 2,000 µm. The particle size is reflected on the thickness of the skeleton of the produced macroporous substrate and the pore size of the macropores 21. Therefore, when the particle size is adjusted to fall within the above range, the thickness of the skeleton of the macroporous substrate and the pore size of the macropores 21 are readily adjusted to fall within preferred ranges. No particular limitation is imposed on the method for preparing the engineering plastic particles. Examples of the preparation method include a method in which a granular or powdery engineering plastic raw material is subjected to sieve classification, to thereby prepare particles having a desired particle size; a method in which a fibrous or tubular engineering plastic material is cut into columnar or tubular particles having an appropriate length; and a method in which an engineering plastic material is pulverized or crushed to form granules or powder, followed by sieve classification, to thereby prepare particles having a desired particle size. When a tubular engineering plastic material is cut into tubular particles for use, voids provided between the welded particles serve as the macropores 21, and hollows of the tubular particles also serve as the macropores 21. Therefore, the tubular particles preferably have an outer diameter of 400 to 2,000 µm, an inner diameter of 200 to 1,800 µm, and a length of 400 to 2,000 µm.

In step (B), the engineering plastic particles prepared through step (A) are placed into a mold and heated, to thereby produce a macroporous substrate. The particles placed into the mold may be heated without any pretreatment, or may be heated after packing of the particles in the mold through several times of tapping. When the packing density of the particles is lower, the macropores 21 having larger pore size are more easily provided. The heating temperature and the heating time are appropriately determined so that the engineering plastic particles can be welded together.

The macroporous substrate, which is produced through the granule joining method, is formed of a single material (i.e., solely the engineering plastic material), wherein the engineering plastic particles are joined together while the particles maintain their shapes, and the macropores 21 correspond to voids provided between the welded engineering plastic particles.

The macroporous substrate production process using the granule joining method (2) may employ the soluble material employed in the macroporous substrate production process using the pressure molding method (1). Specifically, after step (A), the engineering plastic particles are mixed with the soluble material employed in the production process (1) described above, and the resultant mixture is placed into a mold and heated in the same manner as step (B), to thereby produce a macroporous substrate. When the soluble material is employed in the production process using the granule joining method (2), voids resulting from elution of the soluble material and voids provided between the particles serve as the macropores 21. The granule joining method employed for the macroporous substrate production process differs from the pressure molding method in that the particles placed in the mold are not subjected to pressure molding. Therefore, the size of voids provided between the engineering plastic particles in the granule joining method tends to become larger than that in the pressure molding method.

Now will be described process 1 of producing a macroporous substrate by the thermal melting-stacking method (3).

In process 1, an engineering plastic material forming the biological implant 1 is added to a material container of a shaping apparatus, the engineering plastic material is heated so as to have fluidity, and the heated material is extruded through a nozzle for patterning, to thereby form a three-dimensional structure having a plurality of voids; i.e., a macroporous substrate.

The engineering plastic material is heated to have fluidity so that it is readily extruded through a nozzle and is readily molded. For example, the engineering plastic material is heated at a temperature falling within a range of the melting point of the engineering plastic material and the decomposition temperature thereof. One or more nozzles may be employed. In an exemplary process for forming a three-dimensional structure, firstly, the engineering plastic material is extruded while a nozzle or a shaping table is moved, and a pattern (e.g., a maze-like pattern) is drawn in a unicursal fashion, to thereby form a first shaped layer. Subsequently, the shaping table is rotated by a specific angle or moved in a horizontal direction by a specific distance, and the same pattern is drawn on the first shaped layer, to thereby form a second shaped layer. A plurality of shaped layers are formed and stacked in the same manner, to thereby produce a three-dimensional porous structure. No particular limitation is imposed on the pattern, and an appropriate pattern may be selected. The stacked layers may have the same pattern or different patterns. The shape, size, arrangement, etc. of the macropores 21 can be controlled through appropriate determination of the pattern. The thickness of the skeleton of the resultant macroporous substrate can be adjusted by appropriately determining the thickness of the engineering plastic material extruded through the nozzle.

The macroporous substrate, which is produced through the thermal melting-stacking method, is formed of a single material (i.e., solely the engineering plastic material), wherein the macropores correspond to voids provided between lines formed by extrusion of the engineering plastic material through the nozzle.

Now will be described process 1 of producing a macroporous substrate by the mesh stacking method (4).

In process 1, at least two mesh sheets which have been preliminarily formed from the engineering plastic material are stacked, and the stacked mesh sheets are heated at a specific temperature, to thereby weld the mesh sheets. No particular limitation is imposed on the network pattern of the mesh sheet, and the network pattern may be, for example, a grid-like, streak, or spiral pattern. The stacked mesh sheets may have the same network pattern or different network patterns. When the stacked mesh sheets have the same network pattern, the respective mesh sheets may be rotated or moved in parallel, such that voids serving as the macropores 21 form complicated paths, rather than cylindrical tubes penetrating between one end of the macroporous substrate and the other end thereof. When mesh sheets having different opening sizes are irregularly stacked, macropores 21 having different pore sizes can be readily provided. No particular limitation is imposed on the heating temperature, so long as the respective mesh sheets are welded.

The macroporous substrate, which is produced through the mesh stacking method, is formed of a single material (i.e., solely the engineering plastic material), wherein the macropores correspond to voids provided between the stacked mesh sheets.

In process 2, a surface portion of the macroporous substrate produced through process 1 is transformed into a porous structure, to thereby form a micropore structural portion 3 having micropores 31.

Process 2 includes process (I) of preparing a surface porous substrate by providing pores in the surface of the macroporous substrate produced through process 1, and process (II) of providing desired micropores 31 by further eroding the surface of the surface porous substrate. Process (I) includes a swelling step of immersing the macroporous substrate produced through process 1 in a swelling solution for swelling the engineering plastic material, and a solidification step of solidifying and washing the macroporous substrate with a liquid which does not elute the engineering plastic material. Process (II) includes a foaming agent holding step of immersing the surface porous substrate prepared through process (I) in a solution containing a foaming agent, to thereby prepare a foaming agent-holding substrate; a surface softening and foaming step of immersing the foaming agent-holding substrate in a foaming solution which causes swelling of the engineering plastic material and foaming of the foaming agent, to thereby prepare a surface-softened, foamed substrate; and a second solidification step of immersing the surface-softened, foamed substrate in a solidification solution which solidifies the swollen engineering plastic material, to thereby prepare a surface foamed substrate.

In process (I), a surface portion of the macroporous substrate produced through process 1 is provided with pores having a pore size equal to or smaller than that of the small-size pores 32 contained in the micropores 31, to thereby prepare a surface porous substrate. Firstly, the swelling step is performed; i.e., the macroporous substrate is immersed in a swelling solution. No particular limitation is imposed on the swelling solution, and an aqueous acid solution, such as sulfuric acid, nitric acid, or chromic acid, may be employed. The swelling step is performed under appropriate conditions for swelling the surface of the macroporous substrate, and the conditions are appropriately determined depending on, for example, the thickness or pore size required for the microporous layer 5. For example, the concentration of the swelling solution affects the porosity and thickness of the microporous layer 5. In general, high concentration is preferred, and concentrated sulfuric acid or concentrated nitric acid is preferably employed. The swelling solution is employed in such an amount that a portion of the macroporous substrate to be eroded is immersed therein. When pores are provided in the entire surface of the macroporous substrate (including the wall surfaces of the pores), the swelling solution is employed in such an amount that the entire macroporous substrate can be immersed therein. The macroporous substrate immersed in the swelling solution may be allowed to stand still therein, or the swelling solution may be stirred. Alternatively, a defoaming treatment may be carried out by reducing the pressure in a container containing the macroporous substrate and the swelling solution, so that the solution enters the interior of the macroporous substrate. The immersion time is determined depending on the amount of erosion. The temperature of the swelling solution is generally adjusted to about ambient temperature.

Subsequently, the solidification step is carried out; i.e., the macroporous substrate removed from the swelling solution is solidified and washed with a liquid which does not elute the engineering plastic material. In the solidification step, the macroporous substrate is washed with a liquid until the liquid becomes neutral, and the engineering plastic material which has been gelled (in some cases, partially dissolved) with the swelling solution is solidified, to thereby prepare a surface porous substrate. The solidification step employs a liquid which does not elute the engineering plastic material (solidification solution). The temperature of the solidification solution is generally adjusted to about ambient temperature. While the surface-swollen macroporous substrate is immersed in the solidification solution for a specific period of time, the macroporous substrate is allowed to stand still therein, the solution is stirred, or the defoaming treatment is carried out. The type, concentration, and temperature of the solidification solution are appropriately determined so as to enhance the diffusion rate of the swelling solution, whereby the porosity and thickness of the microporous layer 5 can be adjusted. Examples of the liquid which does not elute the engineering plastic material include water and ethanol.

The thickness of a region of the surface porous substrate in which pores are provided may be equal to that of the microporous layer 5 of the biological implant 1. Pores of the surface porous substrate may have such a pore size that the foaming agent employed in process (II) can enter the pores. The pore size is appropriately determined depending on the type of the foaming agent employed. The thickness of the region containing pores and the pore size of the pores can be adjusted by controlling, for example, the time for immersion in the swelling solution, the time for immersion in the liquid which does not elute the engineering plastic material, and/or the immersion temperature.

Process (I) may optionally include a step of drying the resultant surface porous substrate. The drying step is carried out under such conditions that, for example, the engineering plastic material does not melt. For example, the drying step is carried out at a temperature lower than the melting point of the engineering plastic material, preferably at a temperature lower than the glass transition temperature of the engineering plastic material.

In process (II), the surface porous substrate prepared through process (I) is eroded again to provide desired micropores 31. Firstly, the foaming agent holding step is performed; i.e., the surface porous substrate prepared through process (I) is immersed in a solution containing a foaming agent, to thereby prepare a foaming agent-holding substrate. This step may employ any foaming agent that can foam in the below-described foaming solution. Examples of the foaming agent include inorganic foaming agents, such as carbonate salts and aluminum powder; and organic foaming agents, such as azo compounds and isocyanate compounds. The foaming agent is preferably a substance which does not adversely affect a living organism when the biological implant 1 is embedded therein. Examples of the substance include carbonate salts, such as sodium hydrogencarbonate, sodium carbonate, and potassium carbonate. No particular limitation is imposed on the solvent which dissolves such a foaming agent, and, for example, water is employed. In the foaming agent holding step, conditions are appropriately determined for holding the foaming agent on the surface of the foaming agent-holding substrate and on the wall surfaces of pores provided through process (I); for example, the concentration of the foaming agent and the amount of the solution employed. The temperature of the solution containing the foaming agent is generally adjusted to about ambient temperature. While the surface porous substrate is immersed in the solution containing the foaming agent, the substrate may be allowed to stand still therein, the foaming solution may be stirred, or the defoaming treatment may be carried out. The immersion time is appropriately determined.

Subsequently, the surface softening and foaming step is carried out; i.e., the foaming agent-holding substrate is immersed in a foaming solution which causes swelling of the engineering plastic material and foaming of the foaming agent, to thereby prepare a surface-softened, foamed substrate. Although this step is generally performed without drying the foaming agent-holding substrate, the foaming agent-holding substrate may be dried. When the foaming agent-holding substrate is immersed in the foaming solution, swelling of the engineering plastic material proceeds in parallel with foaming of the foaming agent, to thereby prepare a surface-softened, foamed substrate. The foaming solution may be any one having the aforementioned characteristics; for example, an aqueous acid solution, such as concentrated sulfuric acid, hydrochloric acid, or nitric acid. When the engineering plastic material is PEEK and the foaming agent is a carbonate salt, the foaming solution is preferably concentrated sulfuric acid having a concentration of 90% or more. The surface softening and foaming step is carried out under immersion conditions that can cause swelling of the engineering plastic material and foaming of the foaming agent. The temperature of the foaming solution is generally adjusted to about ambient temperature. While the foaming agent-holding substrate is immersed in the foaming solution, the substrate may be allowed to stand still therein, the foaming solution may be stirred, or the defoaming treatment may be carried out. The immersion time is appropriately determined.

Subsequently, the second solidification step is carried out; i.e., the surface-softened, foamed substrate is immersed in a solidification solution which solidifies the swollen engineering plastic material, to thereby prepare a surface foamed substrate. In the second solidification step, the surface-softened, foamed substrate removed from the foaming solution may be immersed in the solidification solution, followed by rinsing off the solidification solution, or the surface-softened, foamed substrate may be repeatedly immersed in the solidification solution several times. The solidification solution employed in this step may be any one which does not elute the engineering plastic material; for example, an aqueous solution, such as water or ethanol, or a polar solution, such as acetone. When the engineering plastic material is PEEK, the solidification solution may be, instead of the aforementioned one, an aqueous inorganic acid solution, such as sulfuric acid having a concentration of less than 90%, nitric acid, phosphoric acid, or hydrochloric acid, or a water-soluble organic solvent. Examples of the water-soluble organic solvent include N-methyl-2-pyrrolidone, dimethylformamide, dimethylacetamide, dimethyl sulfoxide, tetrahydrofuran, alcohols such as ethylene glycol, diethylene glycol, triethylene glycol, propylene glycol, dipropylene glycol, glycerin, ethanol, propanol, butanol, pentanol, and hexanol, aqueous solutions of any of these, liquid polymers such as polyethylene glycol, polypropylene glycol, and polyvinylpyrrolidone, aqueous solutions of any of these, and mixtures of any of these. In the second solidification step, the surface-softened, foamed substrate is immersed in the solidification solution under conditions that can solidify the substrate. For example, the temperature of the solidification solution is generally adjusted to about ambient temperature. While the surface-softened, foamed substrate is immersed in the solidification solution, the substrate may be allowed to stand still therein, the solidification solution may be stirred, or the defoaming treatment may be carried out. The immersion time is appropriately determined.

Process (II) may optionally include a step of washing the surface foamed substrate. In the washing step, the surface foamed substrate is washed with a liquid until the liquid becomes neutral. In the washing step, the surface foamed substrate removed from the solidification solution may be immersed in a washing liquid, followed by rinsing off the washing liquid, or the surface foamed substrate may be repeatedly immersed in the washing liquid several times. The washing liquid employed in the washing step may be any one which does not elute the engineering plastic material; for example, water or pure water. The washing step may be carried out at, for example, ambient temperature.

Process (II) may optionally include a step of drying the resultant surface foamed substrate. The drying step is carried out under such conditions that, for example, the engineering plastic material does not melt. For example, the drying step is carried out at a temperature lower than the melting point of the engineering plastic material, preferably at a temperature lower than the glass transition temperature of the engineering plastic material.

Thus, the surface foamed substrate (which may also be referred to as "surface porous structure"); i.e., the biological implant 1 is produced.

The surface foamed substrate; i.e., the biological implant 1, may be used as produced, or may be molded or formed into a desired shape before use. When the biological implant 1 is used as produced, the macroporous substrate is preferably prepared to have a desired shape.

In the production process of the first embodiment, the porosity of the biological implant 1, the mean pore size of the macropores 21, the mean pore size of small-size pores and medium-size pores of the micropores 31, and the thickness or the like of the microporous layer 5 can be adjusted by appropriately determining, for example, the type, concentration, immersion time, and temperature of the swelling solution and solidification solution employed in process (I), and the foaming-agent-containing solution and solidification solution employed in process (II).

In the biological implant 1 of the first embodiment, the microporous layer 5 has the small-size pores 32 having a mean pore size of less than 10 µm, and the medium-size pores 33 having a mean pore size of 10 to 200 µm. However, the microporous layer may have only small-size pores with substantially no medium-size pores. The microporous layer having only small-size pores can be formed by omitting process (II) from the production process for the biological implant 1 of the first embodiment. Specifically, the microporous layer can be formed through process (I), in which the macroporous substrate produced through process 1 is immersed in the swelling solution, and the thus-swollen macroporous substrate is solidified and washed, to thereby provide pores in the surface of the macroporous substrate.

Second Embodiment

Another embodiment of the biological implant of the present invention will next be described. The biological implant of the second embodiment has the same configuration as the biological implant 1 of the first embodiment, except that macropores having a generally uniform pore size are present. When the biological implant has macropores having a generally uniform pore size, the entire biological implant exhibits uniform strength, resulting in easy quality control.

The presence of macropores having a generally uniform pore size in the biological implant can be determined through observation of a cross section of the biological implant embedded in a resin under a digital microscope. The presence of macropores having a generally uniform pore size in the biological implant can be determined when the resultant image indicates that macropores which are generally entirely surrounded by the macropore structural portion have generally the same pore size, and/or that macropores have a shape which is difficult to specify but a uniform pore size as a whole. The presence of macropores having a shape which is difficult to specify but a uniform pore size as a whole corresponds to, for example, the case where a large number of macropores having a generally uniform pore size are present, and communicating macropores are provided through communication of most of the macropores observed in the image; the case where the macroporous substrate is formed in a regular pattern through the thermal melting-stacking method, and pore-defining portions provided between strands extruded through a nozzle have a uniform pattern as a whole; or the case where the macroporous substrate is formed by regularly stacking mesh sheets having the same opening size through the mesh stacking method, and pore-defining portions provided between mesh skeletons have a uniform pattern as a whole.

The biological implant of the second embodiment can be produced in the same manner as the biological implant 1, except that the aforementioned macroporous substrate production method (1), (3), or (4) is modified as described below.

Production of the macroporous substrate through the pressure molding method (1) is carried out in the same manner as described above, except that a soluble material having a generally uniform particle size (i.e., a soluble material having a narrow particle size distribution) is employed as a pore-providing material.

Production of the macroporous substrate through the thermal melting-stacking method (3) is carried out in the same manner as described above, except that a regular pattern is drawn so as to achieve a generally uniform pore size.

Production of the macroporous substrate through the mesh stacking method (4) is carried out in the same manner as described above, except that mesh sheets having a network pattern with a uniform opening size are regularly stacked.

Third Embodiment

Still another embodiment of the biological implant of the present invention will next be described. The biological implant of the third embodiment has the same configuration as the biological implant 1 of the first embodiment, except that macropores are provided so as to have a pore size which increases from the center of the biological implant toward the exposed surface thereof. When the biological implant has macropores whose pore size increases toward the exposed surface, a biological tissue easily enters the biological implant through macropores which are open at the exposed surface. In addition, even when the pore size of macropores is increased so as to facilitate entrance of a biological tissue, the resultant biological implant can maintain a desired strength.

The biological implant of the third embodiment can be produced in the same manner as the biological implant 1, except that the aforementioned macroporous substrate production method (1), (3), or (4) is modified as described below.

Production of the macroporous substrate through the pressure molding method (1) is carried out in the same manner as described above, except that at least two molded products containing soluble materials (i.e., pore-providing materials) having different particle sizes are formed; a molded product containing a soluble material having a smaller particle size is provided at the center; a molded product containing a soluble material having a larger particle size is provided at the periphery; a specific pressure is applied to these molded products to thereby form a composite molded product; and the composite molded product is heated at a specific temperature.

There are provided at least two molded products containing soluble materials having different particle sizes. The soluble material contained in a molded product may have a particle size which is totally different from or partially the same as that of the soluble material contained in another molded product. The pressure for molding of the molded products or the composite molded product may be such a pressure that the molded product can be maintained its shape during production thereof.

In the case of, for example, press molding, instead of forming at least two molded products containing soluble materials having different particle sizes, a soluble material having a smaller particle size of these soluble materials may be provided at the center, and a specific pressure is applied to the soluble material, to thereby form a single molded product.

Production of the macroporous substrate through the thermal melting-stacking method (3) is carried out in the same manner as described above, except that a pattern is drawn so as to provide macropores having a smaller pore size in the vicinity of the center of the macroporous substrate. Specifically, there are formed a shaped layer with a pattern having lines provided at regular wide intervals, and a shaped layer with a pattern in which the interval between lines increases from the center toward the periphery. For production of the macroporous substrate, these shaped layers are stacked so that the interval between lines at the center of the macroporous substrate is smaller than that between lines in the vicinity of the exposed surface of the substrate.

Production of the macroporous substrate through the mesh stacking method (4) is carried out in the same manner as described above, except that there are employed a plurality of mesh sheets having network patterns with different opening sizes, as well as a single mesh sheet with a smaller opening size at the center and a larger opening size at the periphery. Specifically, a mesh sheet with a smaller opening size at the center and a larger opening size at the periphery is stacked on a mesh sheet having a large opening size, so that openings have a smaller size at the center of the macroporous substrate. Finally, a mesh sheet having a large opening size is stacked, and the resultant stacked product is heated, to thereby weld the mesh sheets together.

Fourth Embodiment

Still another embodiment of the biological implant of the present invention will next be described. The biological implant of the fourth embodiment has the same configuration as the biological implant 1 of the first embodiment, except that macropores are provided so as to have a pore size which decreases from a first surface of the biological implant toward a second surface thereof. In the case where the biological implant has macropores whose pore size decreases from the first surface toward the second surface, when, for example, the biological implant is applied to a site where bonding is required between the biological implant and biological bone, so that the surface of the biological implant having macropores with a larger pore size comes into close contact with the bone, and the surface of the biological implant having macropores with a smaller pore size is directed to a site where a soft tissue easily enters, the biological implant allows the bone tissue to enter therein easily, and can suppress entrance of the soft tissue therein. In addition, even when the pore size of macropores is increased so as to facilitate entrance of the bone tissue, the resultant biological implant can maintain a desired strength.

The biological implant of the fourth embodiment can be produced in the same manner as the biological implant of the third embodiment, except that the pore size of macropores is decreased from a first surface of the biological implant toward a second surface thereof.

Fifth Embodiment

Still another embodiment of the biological implant of the present invention will next be described. The biological implant of the fifth embodiment has the same configuration as the biological implant 1 of the first embodiment, except that a plurality of macropores are provided so as to linearly penetrate between a first surface of the biological implant and a second surface thereof, and the macropores are unidirectionally oriented. Specifically, in the biological implant of the fifth embodiment, the axes of macropores (i.e., through holes) are provided at specific intervals so as to be in parallel with one another. When macropores (through holes) are unidirectionally oriented in the biological implant, a biological tissue (e.g., blood) easily enters the interior of the biological implant via the macropores immediately after embedding of the biological implant in a living organism, and the biological tissue enters the microporous layer formed on the surfaces of the macropores. Thus, osteogenesis is promoted in the interior of the biological implant of the fifth embodiment immediately after embedding of the biological implant in the living organism.

The biological implant can be produced through process 1; i.e., formation of a macroporous substrate having unidirectionally oriented macropores (through holes), and process 2; i.e., formation of a micropore structural portion by transformation of a surface portion of the macroporous substrate into a porous structure.

The biological implant of the fifth embodiment can be produced in the same manner as the biological implant 1, except that the aforementioned macroporous substrate production method (3) or (4) is modified as described below. Specifically, in the same manner as process 2 for producing the biological implant 1 described above, a surface portion of the macroporous substrate is transformed into a porous structure, to thereby form a micropore structural portion. The through holes provided in the macroporous substrate may be independent through holes (i.e., adjacent through holes are independent of each other), or communicating through holes (i.e., adjacent through holes communicate with each other via voids provided in the wall surfaces of the through holes).

Production of the macroporous substrate through the thermal melting-stacking method (3) is carried out in the same manner as described above, except that a pattern is drawn such that a plurality of through holes (macropores) linearly penetrating between a first surface and a second surface are unidirectionally oriented.

When the macroporous substrate has independent through holes (i.e., adjacent through holes are independent of each other), the macroporous substrate is produced through, for example, the following procedure. For formation of a first shaped layer, the material extruded through a nozzle is shaped into a wavy line pattern by reciprocating the nozzle or a shaping table so that unidirectionally aligned wavy lines are drawn in a unicursal fashion so as to come into contact with each other at vertices of concave portions. Specifically, a wavy line is drawn from a first end to a second end and turned at the second end, and then another wavy line is drawn to be in parallel with the previous wavy line so that the wavy lines come into contact with each other at vertices of concave portions. This operation is repeated so that wavy lines are drawn in a unicursal fashion so as to come into contact with each other at vertices of concave portions, to thereby form a pattern in which the lines are connected at both ends. Thus, the first shaped layer is formed in which a plurality of generally circular pores are arranged in a lattice-like pattern. A second shaped layer is formed so as to have the same pattern as the first shape layer and overlap with the first shape layer. A third and subsequent shaped layers are formed in the same manner as described above, to thereby produce a macroporous substrate in which a plurality of independent through holes (macropores) linearly penetrating between a first surface and a second surface are unidirectionally oriented. Subsequently, in the same manner as process 2 for producing the biological implant 1, a surface portion of the resultant macroporous substrate is transformed into a porous structure, to thereby form a micropore structural portion. Thus, the biological implant of the fifth embodiment can be produced.

When the macroporous substrate has communicating through holes (i.e., adjacent through holes communicate with each other), the macroporous substrate is produced through, for example, the following procedure. For formation of a first shaped layer, the material extruded through a nozzle is shaped into a straight line pattern by reciprocating the nozzle or a shaping table so that straight lines are drawn in a unicursal fashion so as to be aligned at specific intervals. Specifically, a straight line is drawn from a first end to a second end and turned at the second end, and then another straight line is drawn to be in parallel with the previous straight line so that the straight lines are spaced from each other at specific intervals. This operation is repeated so that, for example, straight lines having the same length are drawn in a unicursal fashion so as to be spaced from each other at specific intervals, to thereby form a pattern in which all the lines are provided in an imaginary space having a generally quadrangular shape in top view. In this case, the end point of the straight line pattern is located diagonally to the start point thereof. For formation of a second shaped layer, drawing of a line is started from the end point of the first shaped layer, to thereby form the same pattern as the first shaped layer on the first shaped layer so that the straight line pattern of the second shaped layer is orthogonal to that of the first shaped layer. For formation of a third shaped layer, drawing of a line is started from the end point of the second shaped layer, to thereby form the same pattern as the first shaped layer on the second shaped layer so as to overlap with the first shaped layer. This process is repeated to weld a plurality of lines in a grid-like pattern, to thereby produce a macroporous substrate in which a plurality of through holes (macropores) linearly penetrating between a first surface and a second surface are unidirectionally oriented, and adjacent through holes communicate with each other. Subsequently, in the same manner as process 2 for producing the biological implant 1, a surface portion of the resultant macroporous substrate is transformed into a porous structure, to thereby form a micropore structural portion. In this case, when the type, concentration, and immersion time of the swelling solution, and the type, concentration, temperature, and the like of the solidification solution are appropriately modified, a wall of a microporous layer having a plurality of micropores can be formed in a void used for communication of unidirectionally penetrating through holes by swelling the wall surface of the void. Thus, modification of the conditions for process 2 achieves production of a biological implant in which the wall surfaces of through holes are entirely formed of microporous layers.

Production of the macroporous substrate through the mesh stacking method (4) is carried out in the same manner as described above, except that a plurality of mesh sheets having the same network pattern are stacked, and the mesh sheets are stacked and welded so that the network patterns thereof are overlapped with one another.

When the macroporous substrate has independent through holes (i.e., adjacent through holes are independent of each other), the macroporous substrate is produced through, for example, the following procedure. Mesh sheets are stacked, each of which has a network pattern wherein circular, elliptic, or polygonal (e.g., triangular or rectangular) voids are arranged in a grid-like or lattice-like fashion, so that the network patterns are not misaligned. The thus-stacked mesh sheets are welded together. This process produces a macroporous substrate in which independent columnar through holes penetrate between a first surface of the substrate and a second surface thereof, and the through holes are unidirectionally oriented. Subsequently, in the same manner as process 2 for producing the biological implant 1, a surface portion of the resultant macroporous substrate is transformed into a porous structure, to thereby form a micropore structural portion. Thus, the biological implant of the fifth embodiment can be produced.

When the macroporous substrate has communicating through holes (i.e., adjacent through holes communicate with each other), the macroporous substrate is produced through, for example, the following procedure. Mesh sheets are stacked, each of which has a network pattern wherein circular, elliptic, or polygonal (e.g., triangular or rectangular) voids are arranged in a grid-like or lattice-like fashion, and has a non-uniform thickness (e.g., having a plurality of protrusions extending in a direction orthogonal to the plane mesh sheet), so that the network patterns are not misaligned. The thus-stacked mesh sheets are welded together, whereby a dent between adjacent protrusions provides a void for communication of through holes. This process produces a macroporous substrate in which a plurality of columnar through holes penetrating between a first surface of the substrate and a second surface thereof are unidirectionally oriented, and adjacent through holes communicate with each other. Subsequently, in the same manner as process 2 for producing the biological implant 1, a surface portion of the resultant macroporous substrate is transformed into a porous structure, to thereby form a micropore structural portion. In this case, when the type, concentration, and immersion time of the swelling solution, and the type, concentration, and temperature of the solidification solution are appropriately modified, a wall of a microporous layer having a plurality of micropores can be formed in a void used for communication of unidirectionally penetrating through holes by swelling the wall surface of the void. Thus, modification of the conditions for process 2 achieves production of a biological implant in which the wall surfaces of through holes are entirely formed of microporous layers.

Sixth Embodiment

Still another embodiment of the biological implant of the present invention will next be described. The biological implant of the sixth embodiment has basically the same configuration as the biological implant 1 of the first embodiment, except that a bioactive substance and/or a drug is supported on the surface of the micropore structural portion.

In the biological implant of this embodiment, a bioactive substance, a drug, or a drug-supporting bioactive substance is supported on the entirety or a portion of the surface of the micropore structural portion; i.e., the exposed surface of the microporous layer and the wall surfaces of micropores. The bioactive substance or the drug-supporting bioactive substance may be supported in the form of film or layer on, for example, the exposed surface of the microporous layer. Alternatively, the bioactive substance or the drug-supporting bioactive substance may be dispersedly supported. When the bioactive substance or the like is supported in the form of film or layer, the bioactive substance or the like preferably has a thickness of, for example, 0.1 to 100 µm, particularly preferably 0.5 to 50 µm. When the bioactive substance or the like is dispersedly supported, the bioactive substance or the like may be in a form which can be supported on the exposed surface of the microporous layer or on the wall surfaces of micropores; for example, particulate, granular, powdery, or agglomerated form. For example, the bioactive substance or the like may have a spherical, oval spherical, acicular, columnar, rod-like, plate-like, or polygonal shape. In such a case, the bioactive substance or the like preferably has a particle size, for example, 0.001 to 10 µm, particularly preferably 0.01 to 5 µm. Unless otherwise specified, the terms "particle" and "particle size" as used herein refer to "primary particle" and "primary particle size," respectively. When the bioactive substance supported on the microporous layer is in agglomerated form, the term "particle" refers to a primary particle; i.e., a minimum unit of the agglomeration, and the term "particle size" refers to the particle size of the primary particle. The particle size can be determined through the intercept method. Specifically, particles are micrographed with a scanning electron microscope, a straight line is drawn across at least 15 particles, and the lengths of the straight line segments on the particles are measured. The thus-measured values are averaged to determine the particle size. In the case of a non-spherical particle, the diameter of the particle is calculated on the basis of the area of a micrograph cross-section thereof.

No particular limitation is imposed on the bioactive substance, so long as it has high affinity to a living organism, and can chemically react with biological tissues, such as bone tissues (including biological bone) and dental tissues (including biological tooth) (hereinafter these tissues may be collectively referred to as "bone tissue"). Examples of the bioactive substance include a calcium phosphate compound, bioactive glass, and calcium carbonate. Specific examples of the calcium phosphate compound include calcium hydrogenphosphate, calcium hydrogenphosphate hydrate, calcium dihydrogenphosphate, calcium dihydrogenphosphate hydrate, α-tricalcium phosphate, β-tricalcium phosphate, dolomite, tetracalcium phosphate, octacalcium phosphate, hydroxyapatite, fluorapatite, carbonate apatite, and chlorapatite. Examples of the bioactive glass include bioglass and crystallized glass (which may also be referred to as "glass-ceramics"). Specific examples of the bioglass include $SiO_2$—$CaO$—$Na_2O$—$P_2O_5$ glass, $SiO_2$—$CaO$—$Na_2O$—$P_2O_5$—$K_2O$—$MgO$ glass, and $SiO_2$—$CaO$—$Al_2O_3$—$P_2O_5$ glass. Specific examples of the crystallized glass include $SiO_2$—$CaO$—$MgO$—$P_2O_5$ glass (which may also be referred to as "apatite-wollastonite crystallized glass") and $CaO$—$Al_2O_3$—$P_2O_5$ glass. These calcium phosphate compounds, bioglass, and crystallized glass are detailed in, for example, "Chemical Handbook, Applied Chemistry, Sixth Edition" (The Chemical Society of Japan, published on Jan. 30, 2003, MARUZEN Co., Ltd.) and "Clinical Application and Development of Bioceramics" (written and edited by Hideki Aoki, et al., Apr. 10, 1987, Quintessence Publishing Co., Ltd.).

Of these bioactive substances, preferred is at least one of a calcium phosphate compound and bioactive glass, which exhibit excellent bioactivity. Particularly preferred is hydroxyapatite or tricalcium phosphate, since it has a composition, a structure, and characteristics similar to those of biological bone, exhibits excellent stability in the body, and has no considerable solubility in the body.

Any drug may be employed depending on the function required for the biological implant of the present invention. Examples of the drug include an anti-inflammatory drug, an antibiotic, an antithrombotic drug, an antitumor agent, an anticoagulant, a vascular cell growth promoter, a vascular cell growth inhibitor, an anticancer drug, a vasodilator, and an osteogenesis induction factor. The osteogenesis induction factor may be any osteogenesis-related protein which is an extract from bone tissue. Examples thereof include a bone morphogenetic protein (BMP), a transforming growth factor (TFG-β), a cartilage-derived morphogenetic protein (CDMP), an osteoinduction factor (OIF), an insulin-like growth factor (IGF), a platelet-derived growth factor (PDFG), and a fibroblast growth factor (FGF). Two or more drugs selected from these may be supported on the surface layer 5, so long as the drugs do not react with one another.

The biological implant containing a bioactive substance is particularly effective for use in a site where the biological implant is required to be bonded to a biological tissue (e.g., bone or skin), since the bioactive substance binds to bone or adsorbs biomolecules. For example, when the biological implant is employed as artificial bone, it readily binds to the bone of a living organism, whereas when the biological implant is employed as a transdermal device, it readily adheres to the skin. When the biological implant contains a drug, the effect of the drug is obtained over a long period of time, since the drug is released over a long period of time. When the biological implant contains a drug layer formed of a drug-supporting bioactive substance, both the effects of the bioactive substance and the drug are obtained. In order to facilitate release of a drug, the drug is preferably provided in the form of drug layer of a drug-supporting bioactive substance and supported on the surface porous structure, rather than being supported directly on the surface porous structure. The bioactive substance and/or the drug layer is preferably supported on the exposed surface of the microporous layer and on the wall surfaces of micropores so as not to block the open micropores.

Next will be described an exemplary method for producing the biological implant of the sixth embodiment.

The biological implant of the sixth embodiment has basically the same configuration as the biological implant 1 of the first embodiment, except that a bioactive substance, a drug, or a drug layer is supported on the exposed surface of the microporous layer of the surface porous structure and on the wall surfaces of micropores. Therefore, the surface porous structure, which has the macropore structural portion and the micropore structural portion, can be produced in basically the same manner as the biological implant of the first embodiment. Next will be described a method for supporting a bioactive substance, a drug, or a drug layer on the exposed surface of the microporous layer of the surface porous structure and on the wall surfaces of micropores.

Now will be described a method for supporting a bioactive substance on the surface porous structure produced in the same manner as the biological implant of the first embodiment.

Firstly, an ultrasonic application step is performed. Specifically, while the surface porous structure is immersed in a bioactive substance suspension, ultrasonic wave is applied to the surface porous structure. Through the ultrasonic application step, the suspension enters the macropores (i.e., the deep portion of the macropore structural portion), to thereby prepare a bioactive substance-deposited substrate in which the bioactive substance enters (preferably evenly) not only the exposed surfaces of the micropores, but also the wall surfaces of the micropores. Ultrasonic wave is applied to the surface foamed substrate immersed in the suspension by means of, for example, an ultrasonic vibrator or an ultrasonic homogenizer. Ultrasonic application conditions are appropriately determined depending on, for example, the pore size or the porosity. For example, an ultrasonic wave (frequency: 20 to 38 kHz, output: 200 W) is applied for 8 to 15 minutes. In the ultrasonic application step, the surface porous structure, which is immersed in the suspension, may be allowed to stand still in the suspension, or the suspension may be stirred. In the ultrasonic application step, the suspension may be stirred for a while after application of the ultrasonic wave, or the bioactive substance-deposited substrate may be immersed in the same type of solvent after application of the ultrasonic wave and the solvent may be stirred for a while.

No particular limitation is imposed on the temperature of the suspension (i.e., the immersion temperature) and the ultrasonic application time in the ultrasonic application step. These conditions may be appropriately determined depending on the amount of the bioactive substance deposited on the surface porous structure. For example, the immersion temperature may be adjusted to be a temperature lower by 30° C. than the glass transition temperature of the thermoplastic resin forming the surface porous structure; specifically, a temperature equal to or lower than the boiling point of the solvent employed. The ultrasonic application time may be one minute to 24 hours. No particular limitation is imposed on the volume of the surface porous structure immersed in the suspension, but the volume is preferably adjusted to 0.001 to 50 $cm^3$ relative to 100 mL of the suspension, since an insufficient amount of the suspension may reduce the amount of the bioactive substance deposited on the surface porous structure.

The suspension employed in the ultrasonic application step contains the aforementioned bioactive substance. No particular limitation is imposed on the medium for suspending the bioactive substance, so long as it does not dissolve the engineering plastic material. Examples of the medium include alcohols, such as methanol, ethanol, and propanol, water, acetone, and hexane. The bioactive substance is preferably in the form of particles having the aforementioned particle size and shape. The suspension is prepared by homogeneously suspending the bioactive substance in a medium. Specifically, the suspension is prepared by adding the bioactive substance in a medium, and stirring the mixture through optional application of an ultrasonic wave (frequency: 20 to 38 kHz, output: 200 W) or optional homogenization with an ultrasonic homogenizer. The amount of the bioactive substance added may be appropriately determined depending on the amount of the bioactive substance deposited in pores. For example, the amount of the bioactive substance may be adjusted to 0.01 to 100 g relative to 100 mL of the medium. The ultrasonic application time may be adjusted so that the bioactive substance can be dispersed homogeneously; for example, 5 to 180 minutes.

The production method employed in this embodiment may optionally include a washing step of washing the bioactive substance-deposited substrate after removal thereof from the suspension. No particular limitation is imposed on the medium employed for washing of the bioactive substance-deposited substrate, so long as it does not dissolve the plastic material. The medium may be, for example, water or the same medium as used for the suspension, and is preferably water or pure water. The washing step may optionally be followed by a drying step of drying the bioactive substance-deposited substrate. No particular limitation is imposed on the drying method, and any method known in the art may be employed. Examples of the drying method include air drying, blow drying, and thermal drying. When the drying step involves heating, the heating temperature is adjusted to be lower than the glass transition temperature of the plastic material.

In the production method employed in this embodiment, subsequently, a fixation step is performed. Specifically, the bioactive substance-deposited substrate is heated at a temperature equal to (the glass transition temperature of the engineering plastic material−30° C.) or higher and lower than the melting point of the engineering plastic material, for supporting and fixation of the bioactive substance. Through the fixation step, the bioactive substance can be further strongly supported and fixed on the exposed surface of the microporous layer and on the wall surfaces of micropores. In the fixation step, the heating temperature is equal to or higher than (the glass transition temperature (Tg) of the engineering plastic material−30° C.); i.e., (Tg−30)° C., and lower than the melting point of the engineering plastic material. When the bioactive substance-deposited substrate is heated at a temperature falling with the above range, a portion of the bioactive substance-deposited substrate is softened in the vicinity of the exposed surface and the wall surfaces, and the deposited bioactive substance is strongly supported, bonded, and fixed. The lower limit of the heating temperature is (Tg−30°) C. For further strong adhesion between the bioactive substance-deposited substrate and the bioactive substance, the heating temperature is preferably equal to or higher than the glass transition temperature (Tg), and particularly preferably (the glass transition temperature (Tg)+40)° C. The upper limit of the heating temperature is adjusted to be lower than the melting point of the engineering plastic material. For further strong adhesion between the surface porous structure and the bioactive substance, the heating temperature is preferably (the glass transition temperature (Tg)+80)° C. As used herein, the glass transition temperature (Tg) of the engineering plastic material refers to the lowest glass transition temperature when the engineering plastic material has a plurality of glass transition temperatures.

In the fixation step, the time for heating the bioactive substance-deposited substrate; i.e., the time during which the substrate is maintained at the aforementioned heating temperature, is adjusted to such a period that a portion of the bioactive substance-deposited substrate can be softened in the vicinity of the exposed surface and the wall surfaces. For further strong adhesion between the bioactive substance-deposited substrate and the bioactive substance, the heating time is preferably one hour or longer, particularly preferably three hours or longer. No particular limitation is imposed on the maximum heating time. Even when the heating time is considerably prolonged, adhesion of the bioactive substance is not necessarily improved commensurate with the prolongation. Therefore, in consideration of, for example, economical or working efficiency, the heating time is adjusted to, for example, 24 hours. The bioactive substance-deposited substrate may be heated through an appropriate heating method known in the art. Thus, the bioactive substance provided on the surface of the bioactive substance-deposited substrate can be fixed.

The above-described process produces the biological implant in which the bioactive substance is supported on the exposed surface of the microporous layer and the wall surfaces of micropores. The biological implant may be used as produced. Alternatively, the biological implant may be molded or formed into a desired shape before use in the same manner as the biological implant 1 of the first embodiment.

Now will be described a method for supporting a drug on the surface porous structure produced in the same manner as the biological implant of the first embodiment.

The surface porous structure prepared in process (II) is immersed in a drug-containing solution for a specific period of time, to thereby produce a biological implant in which the drug is supported on the microporous layer of the surface porous structure. The drug may be appropriately selected depending on the required function. For example, at least one of the aforementioned drugs may be selected. When the drug is in the form of liquid, the drug may be used as is or as a diluted solution. Meanwhile, when the drug is in the form of solid, the drug may be used as a drug liquid prepared by dissolving or suspending the drug in an appropriate solvent. The drug concentration of the diluted solution or the drug liquid is appropriately adjusted so as to be equal to or higher than the effective concentration of the drug used, and to fall within a range which does not adversely affect a living organism. No particular limitation is imposed on the time during which the surface porous structure is immersed in the drug-containing solution, so long as the drug is supported on the microporous layer of the surface porous structure. The immersion time is preferably 10 minutes or longer.

When the drug is supported on the surface porous structure, a defoaming treatment is preferably carried out while the surface porous structure is immersed in the drug-containing solution. The defoaming treatment allows the drug to enter macropores and micropores of the surface porous structure. The defoaming treatment can also shorten the time during which the surface porous structure is immersed in the drug-containing solution.

Preferably, the surface porous structure is thoroughly dried at ambient temperature after removal thereof from the drug-containing solution.

Now will be described a method for supporting a drug layer formed of a drug-containing bioactive substance on the surface porous structure produced in the same manner as the biological implant of the first embodiment.

The surface porous structure prepared in process (II) is immersed in both a calcium solution containing at least 10 mM calcium ion and a phosphate solution containing at least 10 mM phosphate ion. At least one of the calcium solution and the phosphate solution contains a drug. Immersion of the surface porous structure in the calcium solution may be preceded or followed by immersion of that in the phosphate solution. Next will be described the case where the surface porous structure is immersed first in the calcium solution.

Firstly, the surface porous structure is immersed in a calcium solution containing at least 10 mM calcium ion for a specific period of time. The calcium solution, which contains at least calcium ion, may contain, for example, sodium ion, potassium ion, magnesium ion, carbonate ion, silicate ion, sulfate ion, nitrate ion, chlorine ion, or hydrogen ion. Preferably, the calcium solution contains substantially no phosphate ion. The calcium solution is generally an aqueous solution of a compound which has high water solubility and does not adversely affect the human body. The calcium solution may be, for example, an aqueous solution of calcium chloride, calcium hydroxide, calcium nitrate, calcium formate, calcium acetate, calcium propionate, calcium butyrate, or calcium lactate, or an aqueous solution of a mixture of any of these compounds. The calcium solution is preferably an aqueous calcium chloride solution.

After having been immersed in the calcium solution for a specific period of time, the surface porous structure is immersed in a phosphate solution containing at least 10 mM phosphate ion. The phosphate solution, which contains phosphate ion, may contain, for example, sodium ion, potassium ion, magnesium ion, carbonate ion, silicate ion, sulfate ion, nitrate ion, chlorine ion, or hydrogen ion. Preferably, the phosphate solution contains substantially no calcium ion. The phosphate solution is generally an aqueous solution of a compound which has high water solubility and does not adversely affect the human body. The phosphate solution may be, for example, an aqueous solution of phosphoric acid, disodium hydrogenphosphate, sodium dihydrogenphosphate, dipotassium hydrogenphosphate, or potassium dihydrogenphosphate, or an aqueous solution of a mixture of any of these compounds. The phosphate solution is preferably an aqueous dipotassium hydrogenphosphate solution.

The drug is contained in at least one of the calcium solution and the phosphate solution. The drug may be appropriately selected depending on the required function. For example, at least one of the aforementioned drugs may be selected. The drug concentration is appropriately adjusted so as to be equal to or higher than the effective concentration of the drug used, and to fall within a range which does not adversely affect a living organism.

No particular limitation is imposed on the order of immersion of the surface porous structure in the aforementioned two aqueous solutions. When, for example, hydroxyapatite serving as a bioactive substance is generated in the interior of the microporous layer (i.e., in the interior of the porous structure), the generation reaction preferably proceeds in an alkaline range in which hydroxyapatite exhibits lower solubility, for increasing the amount of hydroxyapatite generated. Therefore, the solution in which the surface porous structure is immersed preferably has a pH of 8 to 10 (i.e., pH in an alkaline range).

The time during which the surface porous structure is immersed in the calcium solution and the phosphate solution is preferably one minute or longer, particularly preferably three minutes or longer. When the immersion time falls within the above range, calcium ion, phosphate ion, and the drug sufficiently penetrate into the interior of the surface porous structure, and the bioactive substance and the drug can be coprecipitated onto the wall surfaces of micropores in the microporous layer of the surface porous structure. In order to increase the amount of the bioactive substance generated, a process of immersing the surface porous structure in the respective solutions may be repeatedly carried out a plurality of times.

The biological implant of the sixth embodiment can be used for various applications. For example, the biological implant is suitable for use as a medical material required to be bonded to a biological tissue. In particular, the biological implant can be employed for, for example, an artificial bone, an artificial tooth root, an implant for alveolar bone osteogenesis, or a transdermal device. The artificial bone can be used in the form of, for example, a bone prosthetic material, an artificial joint, a bone joining material, an artificial vertebral body, an intervertebral spacer, or a vertebral cage. The implant for alveolar bone osteogenesis is embedded to compensate for thinned alveolar bone. The transdermal device is a medical device which is penetrated through the skin of a living body for alimentation, chemical injection, or blood circulation from the outside to the inside of the body. The transdermal device is provided on any artificial organ.

The biological implant of the present invention is not limited to the above-described embodiments, and various modifications may be made so long as the object of the present invention can be achieved.

EXAMPLES

Example 1

In process 1, a macroporous substrate was produced through the pressure molding method as described below.

Polyether ether ketone (PEEK) (glass transition temperature: 143° C., melting point: 340° C., elastic modulus: 4.2 GPa, flexural strength: 170 MPa) in the form of powder (Vestakeep 4000P, product of Daicel-Evonik Ltd., particle size: 50 to 1,200 µm (mean particle size: 500 µm)) was dry-mixed with sodium chloride (product of Wako Pure Chemical Industries, Ltd., particle size: 100 to 1,000 µm (mean particle size: 500 µm)) serving as a pore-providing material so that the ratio by volume of sodium chloride was 70 vol % with respect to the total volume of PEEK and sodium chloride, to thereby prepare a mixture.

The mixture was placed in a mold and heated to 370° C. While the mold was maintained at the temperature, a pressure of 200 MPa was applied to the mold (i.e., hot pressing) for 10 minutes, to thereby prepare a heated molded product.

Pure water was provided in an amount sufficient for immersion of the entirety of the heated molded product, and the molded product was immersed in the pure water for 24 hours, to thereby elute sodium chloride therein. Thereafter, the resultant product was dried at 120° C. for one hour, to thereby prepare a macroporous substrate having a PEEK skeleton and having a plurality of macropores.

In process 2, a surface portion of the resultant macroporous substrate was transformed into a microporous layer as described below.

Firstly, the macroporous substrate was immersed in concentrated sulfuric acid (concentration: 98%) (30 mL) at ambient temperature for one minute, to thereby swell the macroporous substrate (swelling step). This swelling step was carried out in a vacuum desiccator under reduced pressure. Subsequently, the macroporous substrate removed from concentrated sulfuric acid was immersed in pure water (1,000 mL) at ambient pressure for five minutes. Thereafter, the macroporous substrate was repeatedly washed until the pH of the pure water fell within a neutral range, and the surface-swollen macroporous substrate was washed and solidified (solidification step). The macroporous substrate was dried at 80° C. for 12 hours, to thereby provide pores in the surface of the macroporous substrate. Thus, process 1 was carried out, to thereby prepare a surface porous substrate.

Subsequently, the surface porous substrate was immersed in an aqueous potassium carbonate solution (concentration: 3 M) (100 mL) at ambient temperature for four hours, so that potassium carbonate was held on the surface of the surface porous substrate and in pores thereof, to thereby prepare a foaming agent-holding substrate (foaming agent holding step).

Subsequently, the foaming agent-holding substrate was immersed in concentrated sulfuric acid (concentration: 95%) (30 mL) at ambient temperature for one minute, for swelling of PEEK and foaming of potassium carbonate, to thereby prepare a surface-softened, foamed substrate (surface softening and foaming step). This surface softening and foaming step was carried out in a vacuum desiccator under reduced pressure.

The surface-softened, foamed substrate was immersed in dilute sulfuric acid (concentration: 86%) (30 mL) at ambient temperature for solidification, and the substrate was then removed from dilute sulfuric acid (concentration: 86%) and immersed in pure water (1,000 mL) at ambient pressure for 10 minutes (second solidification step). Thereafter, the resultant product was repeatedly washed until the pH of the pure water fell within a neutral range, followed by drying at 80° C. for 12 hours, to thereby produce a surface foamed substrate; i.e., a biological implant of Example 1.

Example 2

A biological implant of Example 2 was produced in basically the same manner as in Example 1, except that the sodium chloride employed in Example 1 was replaced with sodium chloride prepared through sieve classification and having a particle size of 355 to 840 μm.

Example 3

A biological implant of Example 3 was produced in basically the same manner as in Example 1, except that the PEEK and sodium chloride employed in Example 1 were respectively replaced with PEEK (particle size: 600 to 840 μm) and sodium chloride (particle size: 600 to 840 μm) prepared through sieve classification; a mixture of PEEK and sodium chloride was prepared by adjusting the ratio by volume of sodium chloride to the total volume of PEEK and sodium chloride to 60 vol %; the mixture was placed in a mold and a pressure of 45 MPa was applied to the mold at ambient temperature for 10 seconds, to thereby prepare a molded product; and the molded product was placed in an oven and heated from ambient temperature to 300° C. at a rate of 5° C./min, and then heated to 360° C. at a rate of 2° C./min and maintained at 360° C. for 20 minutes, to thereby prepare a heated molded product.

Example 4

A biological implant of Example 4 was produced in basically the same manner as in Example 3, except that the PEEK was replaced with PEEK having a particle size of 355 to 600 μm, and the sodium chloride was replaced with sodium chloride having a particle size of 355 to 600 μm.

Example 5

A biological implant of Example 5 was produced in basically the same manner as in Example 3, except that the PEEK was replaced with PEEK having a particle size of 150 to 355 μm, and the sodium chloride was replaced with sodium chloride having a particle size of 150 to 355 μm.

Example 6

A biological implant of Example 6 was produced in basically the same manner as in Example 3, except that the PEEK was replaced with PEEK having a particle size of 150 to 355 μm.

Example 7

A biological implant of Example 7 was produced in basically the same manner as in Example 1, except that sodium chloride was not employed; a PEEK tube (product of Nirei Industry Co., Ltd., outer diameter: 1.0 mm, inner diameter: 0.5 mm) was cut into tubular pieces having a length of 1 to 1.5 mm and the pieces were placed in a mold and heated at 355° C. for 30 minutes, to thereby prepare a macroporous substrate through the granule joining method; and the macroporous substrate is immersed in concentrated sulfuric acid for five minutes in the aforementioned "swelling step" for formation of a microporous layer.

Example 8

A biological implant of Example 8 was produced in basically the same manner as in Example 3, except that the PEEK was replaced with PEEK having a particle size of 500 to 710 μm, and the sodium chloride was replaced with sodium chloride having a particle size of 500 to 710 μm.

The mean pore size of macropores and the porosity, which were determined through the methods described below, were 623 μm and 70.0%, respectively.

Example 9

In process 1, a macroporous substrate was produced through the thermal melting-stacking method as described below.

By means of a direct forming apparatus (IMC-1703, product of Imoto Machinery Co., Ltd.), the PEEK powder employed in Example 1 was heated to 420° C., and the resultant product was extruded through a nozzle (diameter: 0.3 mm), to thereby prepare a macroporous substrate having a plurality of PEEK lines welded in a grid-like pattern. Specifically, a straight line (length: 20 mm) was drawn from a first end to a second end and turned at the second end, and then another straight line was drawn to be in parallel with the previous straight line so that the straight lines were spaced from each other at specific intervals. This operation was repeated so that straight lines were drawn in a unicursal fashion so as to be spaced from each other at a pitch of 1.0 mm, to thereby form a pattern in which all the lines were provided in an imaginary space having a generally quadrangular shape in top view. Thus, a first shaped layer was formed. In this case, the end point of the straight line pattern was located diagonally to the start point thereof. For formation of a second shaped layer, drawing of a line was started from the end point of the first shaped layer, to thereby form the same pattern as the first shaped layer on the first shaped layer so that the straight line pattern of the second shaped layer was orthogonal to that of the first shaped layer. For formation of a third shaped layer, drawing of a line was started from the end point of the second shaped layer, to thereby form the same pattern as the first shaped layer on the second shaped layer so as to overlap with the first shaped layer. This process was repeated to stack 30 shaped layers in total, to thereby prepare a macroporous substrate. Subsequently, in process 2, a surface portion of the macroporous substrate was treated in the same manner as in Example 1, to thereby form a microporous layer.

Example 10

A macroporous substrate was prepared in the same manner as in Example 9, except that the pitch was changed to 1.4 mm. Subsequently, in process 2, a surface portion of the macroporous substrate was transformed into a microporous layer in the same manner as in Example 1, except that the macroporous substrate was immersed in concentrated sulfuric acid for five minutes in the swelling step.

Comparative Example 1

PEEK plate material (product of Victrex) was employed as a biological implant.

Referential Example 1

Simulated bone for implantation practice (T6-X.1143F, product of Nissin Dental Products INC.) was employed as a biological implant.
(Determination of Mean Pore Size of Macropores)

Each of the produced biological implants was embedded and fixed in an epoxy resin, followed by cutting of the implant. The cut surface of the implant was micrographed with a digital microscope (at a magnification of 40). Five straight lines were randomly drawn across the micrograph image, and the macropores on the straight lines were used for determination. The lengths of all the straight line segments on the macropores were measured, and the arithmetic mean of the thus-measured values were regarded as the mean pore size of the macropores.
(Porosity)

The porosity of each of the produced biological implants was calculated on the basis of the mass and volume of the biological implant and the specific weight of PEEK (1.30 g/cm$^3$).
(Observation of Biological Implant)

The cut surface of each of the produced biological implants was observed in the same manner as described above in "determination of mean pore size of macropores."

Figure 3:
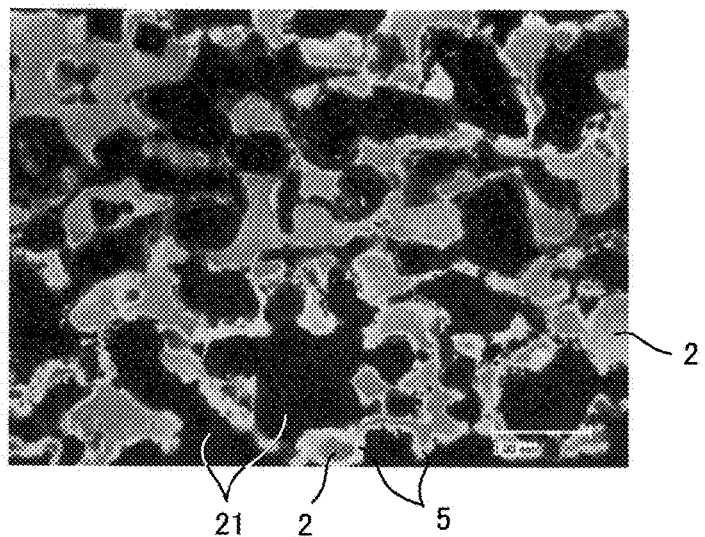
FIG. 3 shows an image of a cross section of a biological implant produced in Example 4, the cross section being observed under a digital microscope.

FIGS. 3 and 4 show micrograph images of the biological implants of Examples 4 and 8, respectively. As illustrated in FIGS. 3 and 4, each of the biological implants of Examples 4 and 8 had numerous macropores 21 defined therein, and a microporous layer 5 formed on the wall surface of each of the macropores 21 and having micropores with a pore size smaller than that of the macropores 21. The macropores 21 had generally circular and generally elliptical pores A having different pore sizes, as well as irregularly shaped pores. The irregularly shaped pores had communicating macropores B provided through communication of a plurality of pores having different pore sizes. The macropore structural portion 2 formed of PEEK was solid. No particulate PEEK was observed in the macropore structural portion 2. The macropore structural portion 2 had a contour defined by the pore-providing material, and had an irregular cross section.

Figure 5:
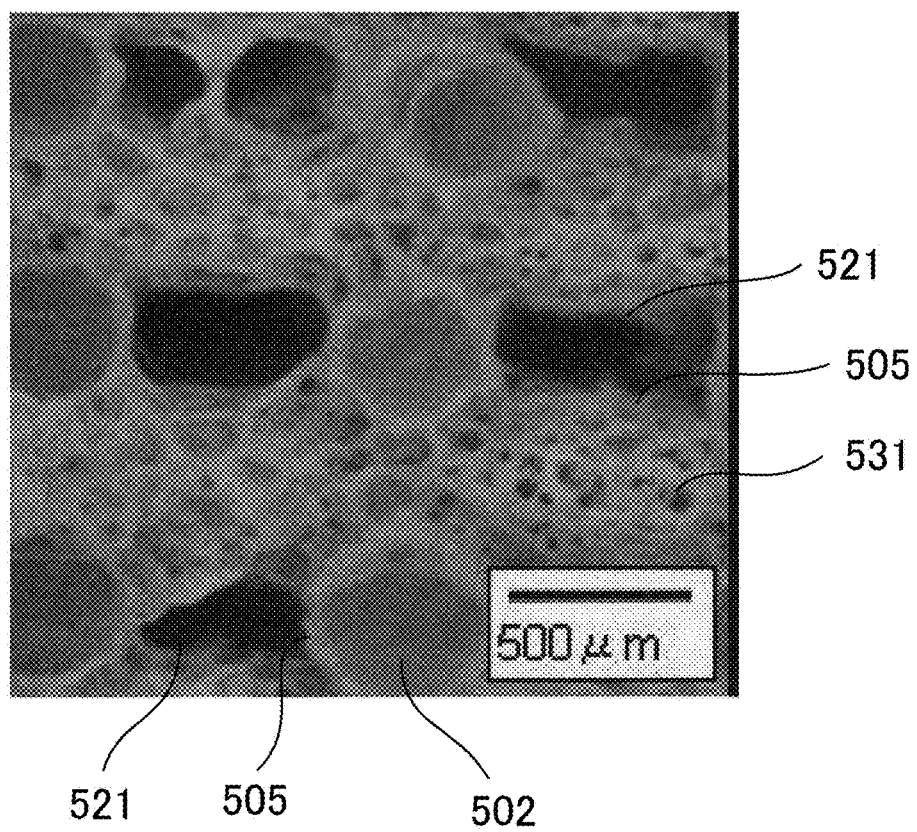
FIG. 5 shows an image of a cross section of a biological implant produced in Example 9, the cross section being observed under a digital microscope.

FIG. 5 shows a micrograph image of the biological implant of Example 9. As illustrated in FIG. 5, the biological implant of Example 9 had numerous macropores 521 having a generally uniform shape and pore size, a solid macropore structural portion 502 was defined by center portions of lines extruded through nozzles, and a microporous layer 505 was formed on the periphery of the macropore structural portion 502 so as to have micropores 531 having a pore size smaller than that of the macropores 521.

Figure 6:
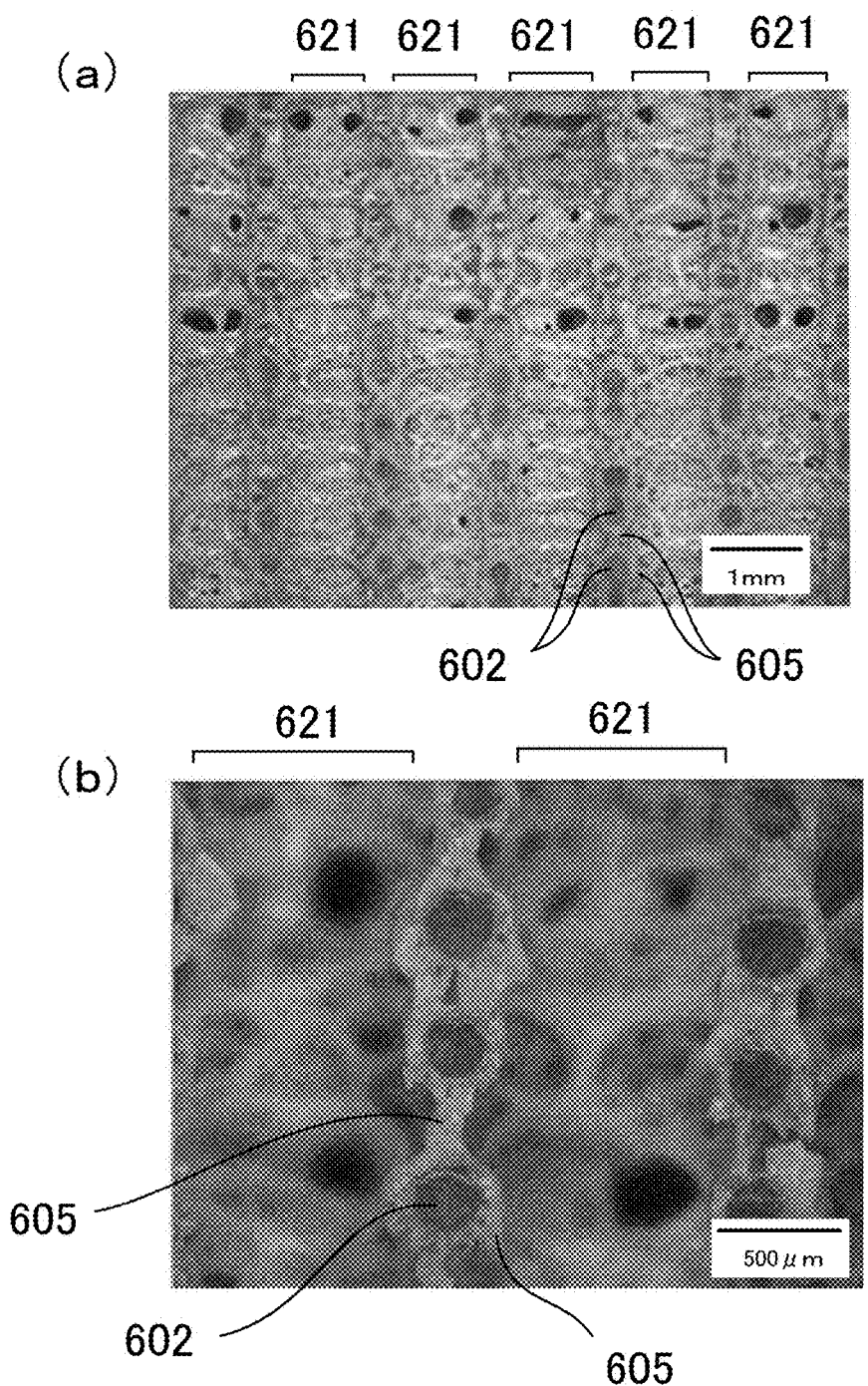
FIG. 6(a) shows an image of a cross section of a biological implant produced in Example 10, the cross section being observed under a digital microscope.
FIG. 6(b) is an enlarged view of a portion of the image shown in FIG. 6(a).

FIG. 6 shows a micrograph image of the biological implant of Example 10. As illustrated in FIG. 6, the biological implant of Example 10 had macropores 621 formed of a plurality of through holes linearly extending from the upper side of the drawing sheet to the lower side thereof. The walls defining the through holes were formed of a solid macropore structural portion 602 defined by center portions of lines extruded through nozzles and a microporous layer 605 provided on the periphery of the macropore structural portion 602 and having micropores. Specifically, the wall of the microporous layer 605 having a plurality of micropores was formed in a void for communicating adjacent through holes in the macroporous substrate by processing the macroporous substrate for formation of the microporous layer.
(Evaluation of Drilling Property)

Under the assumption that each of the produced biological implants was employed as a biological implant for alveolar bone osteogenesis, the ease with which a pilot hole was drilled with a dental drill in the biological implant for insertion of an artificial dental root was evaluated by the below-described maximum torque and maximum load.

Each of the produced biological implants (dimensions: ϕ16×7 mm) was placed on a testing table, and a hole was drilled in the biological implant with a drill (diameter: 3.2 mm) provided in a dental drill engine and rotated at 800 rpm. The maximum of torque of the drill was measured during drilling with the dental drill engine, and the thus-measured value was regarded as the maximum torque. The results are shown in Table 1.

Each of the produced biological implants (dimensions: ϕ16×7 mm) was placed on a load cell, and a hole was drilled in the biological implant with a drill (diameter: 3.2 mm) provided in a dental drill engine and rotated at 800 rpm. The maximum of load imposed on the load cell was measured during drilling with the dental drill engine, and the thus-measured value was regarded as the maximum load. The results are shown in Table 1.

TABLE 1

| | Raw material (particle size) (μm) | Pore-providing material (particle size) (μm) | Porosity (%) | Pore size of macropores (μm) | Production method of macroporous substrate | Production method of microporous layer | Evaluation of drilling property | |
|---|---|---|---|---|---|---|---|---|
| | | | | | | | Maximum torque (N · cm) | Maximum load (N) |
| Ex. 1 | PEEK powder (50 to 1200) | NaCl (100 to 1000) | 70.0 | 512 | Pressure molding method (hot pressing) | 1-minute immersion in concentrated sulfuric acid in swelling step ↓ 1-minute immersion in foaming solution | 4.5 | 34.5 |

TABLE 1-continued

| | Raw material (particle size) (μm) | Pore-providing material (particle size) (μm) | Porosity (%) | Pore size of macropores (μm) | Production method of macroporous substrate | Production method of microporous layer | Maximum torque (N·cm) | Maximum load (N) |
|---|---|---|---|---|---|---|---|---|
| Ex. 2 | PEEK powder (50 to 1200) | NaCl classified (355 to 840) | 70.0 | 485 | Pressure molding method (hot pressing) | 1-minute immersion in concentrated sulfuric acid in swelling step ↓ 1-minute immersion in foaming solution in surface softening and foaming step | 4.3 | 32.2 |
| Ex. 3 | PEEK powder classified (600 to 840) | NaCl classified (600 to 840) | 69.4 | 723 | Pressure molding method (heating after press molding) | 1-minute immersion in concentrated sulfuric acid in swelling step ↓ 1-minute immersion in foaming solution in surface softening and foaming step | 6.3 | 40.3 |
| Ex. 4 | PEEK powder classified (355 to 600) | NaCl classified (355 to 600) | 68.7 | 467 | Pressure molding method (heating after press molding) | 1-minute immersion in concentrated sulfuric acid in swelling step ↓ 1-minute immersion in foaming solution in surface softening and foaming step | 4.0 | 37.0 |
| Ex. 5 | PEEK powder classified (150 to 355) | NaCl classified (150 to 355) | 69.9 | 253 | Pressure molding method (heating after press molding) | 1-minute immersion in concentrated sulfuric acid in swelling step ↓ 1-minute immersion in foaming solution in surface softening and foaming step | 4.3 | 40.7 |
| Ex. 6 | PEEK powder classified (150 to 355) | NaCl classified (600 to 840) | 69.7 | 621 | Pressure molding method (heating after press molding) | 1-minute immersion in concentrated sulfuric acid in swelling step ↓ 1-minute immersion in foaming solution in surface softening and foaming step | 6.3 | 40.7 |
| Ex. 7 | PEEK tube (outer diameter: 1.0 mm, inner diameter: 0.5 mm, length: 1 to 1.5 mm) | None | 50.0 | 1342 | Granule joining method (heating after molding (no pressurization)) | 5-minute immersion in concentrated sulfuric acid in swelling step ↓ 1-minute immersion in foaming solution in surface softening and foaming step | 12.0 | 49.0 |
| Ex. 8 | PEEK powder classified (500 to 710) | NaCl classified (500 to 710) | 70.0 | 623 | Pressure molding method (heating after press molding) | 1-minute immersion in concentrated sulfuric acid in swelling step ↓ 1-minute immersion in foaming solution in surface softening and foaming step | 4.2 | 38.6 |
| Ex. 9 | PEEK powder (50 to 1200) | None | 64.9 | 823 | Thermal melting-stacking method | 1-minute immersion in concentrated sulfuric acid in swelling step ↓ 1-minute immersion in foaming solution in surface softening and foaming step | 8.7 | 22.3 |
| Ex. 10 | PEEK powder (50 to 1200) | None | 74.7 | 1105 | Thermal melting-stacking method | 5-minute immersion in concentrated sulfuric acid in swelling step ↓ 1-minute immersion in foaming solution in surface softening and foaming step | 4.7 | 17.7 |
| Comp. Ex. 1 | PEEK plate material | | 0.0 | — | — | None | 34.0 | 53.0 |
| Ref. Ex. 1 | Simulated bone for implantation practice | | — | — | — | None | 5.3 | 24.0 |

As illustrated in Table 1, the biological implants of Examples 1 to 10 exhibited drilling properties (evaluated by maximum toque and maximum load) comparable to those of the simulated bone for implantation practice of Referential Example 1. In contrast, the biological implant of Comparative Example 1 exhibited a maximum torque and a maximum load higher than those of the simulated bone for implantation practice of Referential Example 1; i.e., the biological implant encountered difficulty in drilling a pilot hole.

DESCRIPTION OF REFERENCE NUMERALS

1: biological implant
2, 502, 602: macropore structural portion
3: micropore structural portion
4: surface porous structure
5, 505, 605: microporous layer
6: exposed surface
21, 521, 621: macropore
22: open macropore
23: inner macropore
24: independent macropore
25: communicating macropore
31, 531: micropore
32: small-size pore
33: medium-size pore

What is claimed is:
1. A biological implant comprising:
a macropore structural portion which defines macropores of the biological implant, wherein the macropores have a mean pore size of 100 μm to 3,000 μm; and a micropore structural portion which has micropores therein, the micropores having a pore size smaller than that of the macropores, the biological implant being characterized in that:

the macropore structural portion is non-microporous;

the micropore structural portion is provided on the surface of the macropores throughout the macropore structural portion;

the macropore structural portion and the micropore structural portion are formed of the same engineering plastic material; and the macropore structural portion is formed of a single material.

2. A biological implant according to claim 1, wherein the macropore structural portion has an irregular cross section.

3. A biological implant according to claim 1, wherein the macropore structural portion is formed through a thermal melting-stacking method or a mesh stacking method.

4. A biological implant according to claim 1, wherein the engineering plastic material is polyether ether ketone.

5. A biological implant according to claim 1 wherein some of the macropores communicate with one another.

6. A biological implant according to claim 1, wherein the micropore structural portion supports a bioactive substance thereon.

* * * * *